(12) United States Patent  (10) Patent No.: US 8,657,550 B2
Ford et al.  (45) Date of Patent: Feb. 25, 2014

(54) CRUCIBLE SHUTTLE ASSEMBLY WITH LINEARLY MOVING CARRIAGE

(75) Inventors: Gordon C. Ford, St. Joseph, MI (US); Raghu Murthy, St. Joseph, MI (US)

(73) Assignee: Leco Corporation, St. Joseph, MI (US)

( * ) Notice: Subject to any disclaimer, the term of this patent is extended or adjusted under 35 U.S.C. 154(b) by 507 days.

(21) Appl. No.: 13/032,844

(22) Filed: Feb. 23, 2011

(65) Prior Publication Data

US 2011/0150609 A1 Jun. 23, 2011

Related U.S. Application Data

(63) Continuation-in-part of application No. 12/055,880, filed on Mar. 26, 2008, now Pat. No. 8,323,565.

(60) Provisional application No. 60/911,320, filed on Apr. 12, 2007.

(51) Int. Cl.
*B65H 1/00* (2006.01)
(52) U.S. Cl.
USPC ............ 414/226.01; 414/222.12; 439/499; 422/64; 422/65; 422/66; 436/48
(58) Field of Classification Search
USPC .................. 414/222.12, 226.01, 226.02; 439/492–499; 422/65, 66, 64; 436/47, 436/48; 403/34–39
See application file for complete search history.

(56) References Cited

U.S. PATENT DOCUMENTS

| | | | |
|---|---|---|---|
| 4,238,450 A | 12/1980 | Bredeweg et al. | |
| 4,456,580 A | 6/1984 | Yamada et al. | |
| 4,573,910 A | 3/1986 | Bredeweg | |
| 5,395,586 A | 3/1995 | Hemzy et al. | |
| 5,441,891 A | 8/1995 | Burkovich et al. | |
| 5,585,068 A | 12/1996 | Panetz et al. | |
| 6,024,925 A * | 2/2000 | Little et al. | 422/65 |
| 6,117,391 A | 9/2000 | Mootz et al. | |
| 6,544,799 B1 * | 4/2003 | Lewis et al. | 436/47 |
| 6,551,833 B1 | 4/2003 | Lehtinen et al. | |
| 6,932,557 B2 * | 8/2005 | Downs et al. | 414/741 |
| 7,390,458 B2 * | 6/2008 | Burow et al. | 422/65 |
| 7,402,280 B2 * | 7/2008 | Ford | 422/65 |
| 7,694,583 B2 * | 4/2010 | Liskow et al. | 73/856 |
| 7,695,239 B2 | 4/2010 | Wu | |
| 2003/0164200 A1 * | 9/2003 | Czeranna et al. | 141/1 |
| 2005/0036864 A1 * | 2/2005 | O'Keeffe | 414/467 |

FOREIGN PATENT DOCUMENTS

GB  2185458 A  * 7/1987

OTHER PUBLICATIONS

US Publication 2008/0253870, published Oct. 16, 2008, to Ford entitled Crucible Shuttle Assembly and Method of Operation.

* cited by examiner

*Primary Examiner* — Gerald McClain
(74) *Attorney, Agent, or Firm* — Price Heneveld LLP

(57) ABSTRACT

A crucible handling shuttle includes a pair of opposed dual crucible-gripping arms mounted on a rotatable head. The shuttle is removably plugged into a sliding block of a carriage to move between a furnace and a crucible loading station. The carriage includes mechanical, electrical, and pneumatic plugs or sockets which couple to mating sockets or plugs of the shuttle. A linear actuator extends between the carriage and the furnace base to raise and lower the carriage and shuttle coupled thereto.

16 Claims, 23 Drawing Sheets

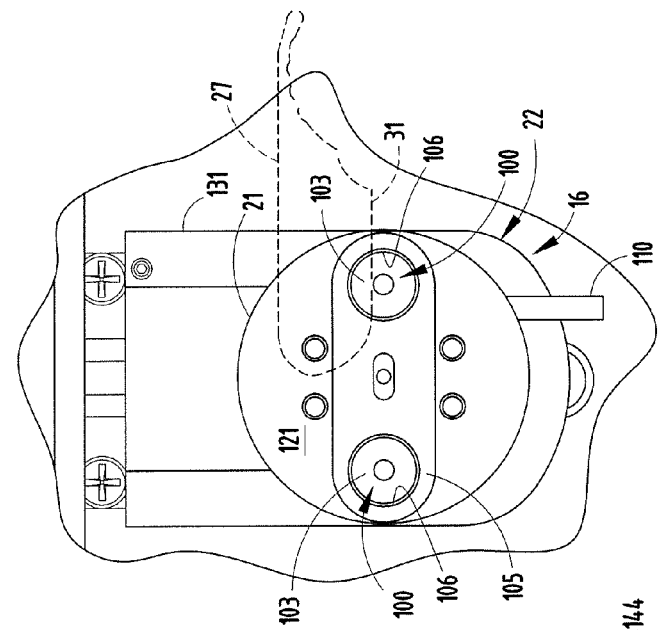
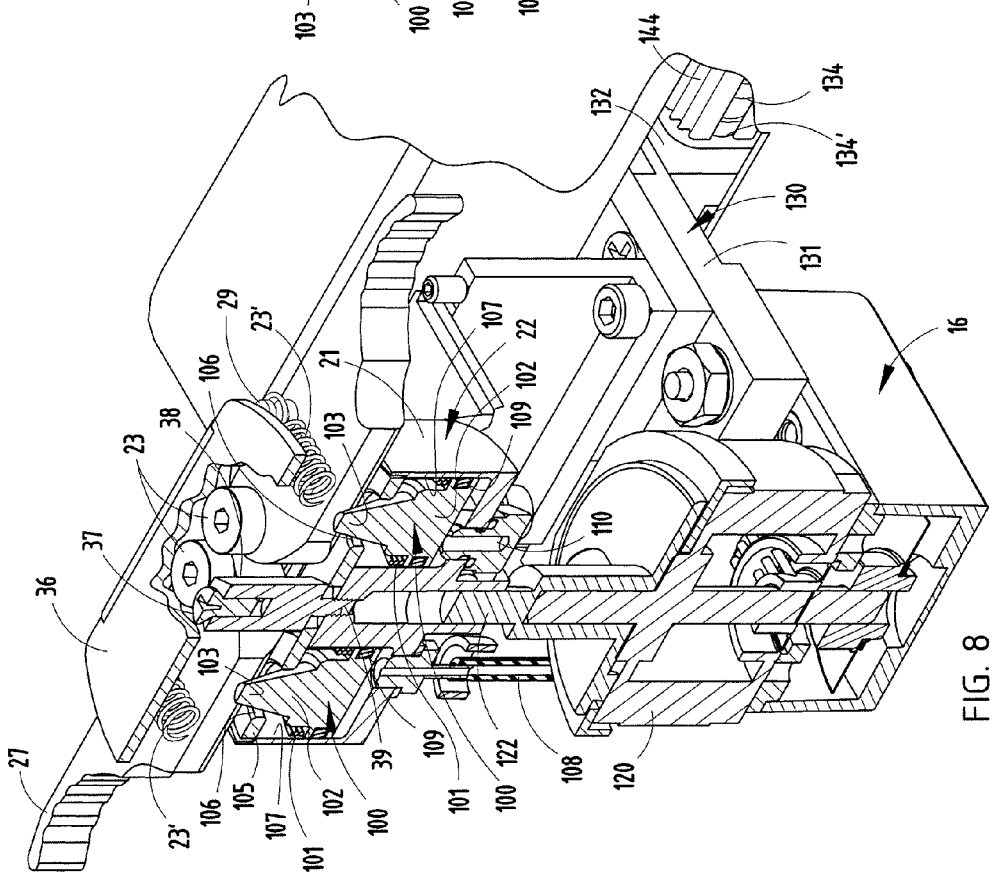

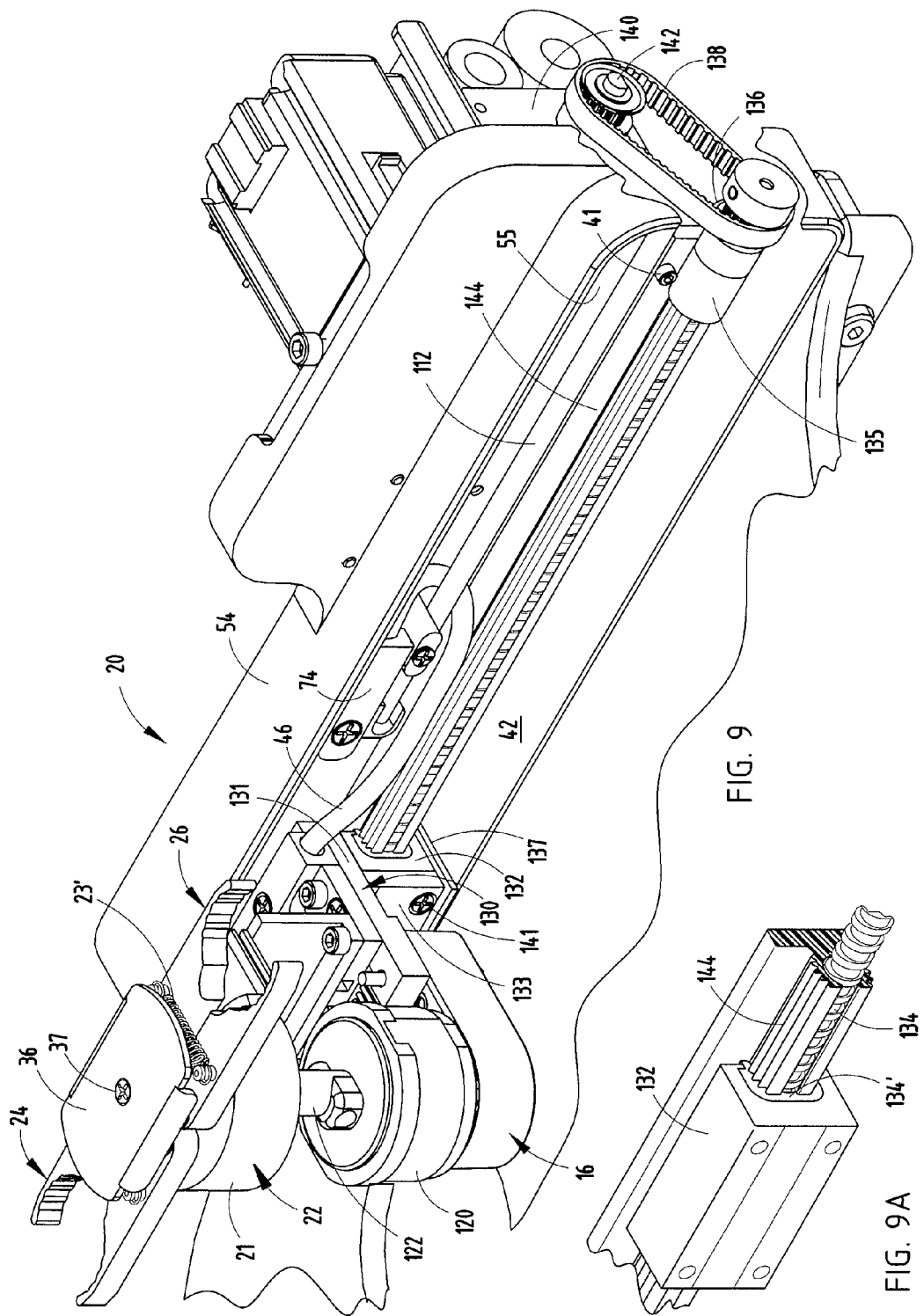

CRUCIBLE SHUTTLE ASSEMBLY WITH LINEARLY MOVING CARRIAGE

CROSS-REFERENCE TO RELATED APPLICATIONS

This application is a continuation-in-part of U.S. patent application Ser. No. 12/055,880 filed on Mar. 26, 2008, which claimed priority under 35 U.S.C. §119(e) on U.S. Provisional Application No. 60/911,320, entitled CRUCIBLE LOADING/UNLOADING ASSEMBLY WITH OPPOSED DUAL GRIPPERS, filed on Apr. 12, 2007, by Gordon C. Ford. The entire disclosures of these applications are incorporated herein by reference.

BACKGROUND OF THE INVENTION

The present invention relates to a crucible loading/unloading assembly for efficiently moving crucibles onto and from an analyzer furnace.

Analyzers are used in the steel industry inter alia for determining the content of carbon and/or sulfur. Such analyzers include, for example, Model No. CS600 which is commercially available from Leco Corporation of St. Joseph, Mich. In the past, several systems have been designed to provide automatic loading and unloading of crucibles into such furnaces to provide more efficient throughput of samples. One such system is represented in, for example, U.S. Pat. No. 4,238,450. Also, sample combustion boats have been the subject of auto-loading, as shown in U.S. Pat. No. 5,395,586. U.S. Pat. No. 7,402,280 also discloses yet another crucible loading system.

Such automated systems represent a significant advance over manually handling of crucibles and particularly spent crucibles and the potential for injury. However such systems either utilize a sequential multi-step process in which a spent crucible is removed and disposed of and subsequently a new crucible is placed on the induction furnace pedestal for introduction into the furnace or do not handle spent crucibles which must be manually removed. Such systems, although preferable to the manual introduction and removal of crucibles, leave room for improvement to increase the throughput of multiple specimens for analysis. The improved crucible handling system disclosed in Ser. No. 12/055,880 (now Publication No. 2008/0253870 A1) has a shuttle which is fixed to a carriage for moving the shuttle between a crucible loading station and the furnace. When used extensively with ceramic crucibles, the gripping arms of the shuttle can become worn requiring replacement. Also the shuttle-to-carriage electrical and pneumatic connections must accommodate the movement of the shuttle and the carriage. The shuttle can only be removed from the carriage with the use of tools and requires a certain amount time and effort.

There remains a need, therefore, for an improved crucible loading and unloading system which allows quick repair and maintenance.

SUMMARY OF THE INVENTION

The system of the present invention accomplishes this goal by providing a crucible handling shuttle having a pair of opposed dual crucible-gripping arms which are mounted on a rotatable platform which is removably mounted to a carriage by a quick disconnect mounting system. The carriage moves the shuttle between a crucible loading station and the furnace and is vertically movable to lift a crucible from the loading station and subsequently lower a crucible into the furnace. One pair of arms picks up a crucible loaded with a preweighed sample, and the shuttle moves to the furnace, where the other pair of arms grip and remove the spent crucible. The shuttle then rotates to deposit the new sample-holding crucible into the furnace. In one embodiment of the invention the carriage moves the shuttle out of the furnace area to a crucible disposal chute positioned between the crucible loading station and the furnace, into which the spent crucible is dropped for disposal. The shuttle is then rotated and raised by the carriage and moved to pick up a new crucible with the same one pair of arms. This method of operation uses the same pair of arms to handle clean crucibles and the other pair of arms to handle spent contaminated crucibles.

Such an assembly provides the capability of handling two crucibles simultaneously for removing a crucible from a furnace and placing a new sample-holding crucible into the furnace. It also disposes of the spent crucible and picks up a new crucible in rapid sequence and while an analysis is being run. The resultant system can be easily maintained by unplugging the shuttle from the carriage and replacing the shuttle with a new one or otherwise provides easy removal of the shuttle for repair.

According to other aspects of the invention, a system is provided for moving articles between at least first and second positions and includes pairs of opposed gripping arms for simultaneously gripping two articles on opposite sides of an axis of rotation, a rotating head supporting said arms, and a linear drive coupled to said rotating platform for moving said gripping arms between a first position and a second position.

According to another aspect of the invention, a method of loading and unloading crucibles to and from a furnace associated with an analyzer includes the steps of picking up a crucible at a loading station with one pair of crucible arms on a shuttle including pairs of opposed crucible-gripping arms for simultaneously gripping crucibles on opposite sides of an axis of rotation, moving the shuttle to a furnace, rotating the pairs of arms, picking up a spent crucible from the pedestal with another pair of arms of the shuttle, and rotating the shuttle and depositing a new crucible in the furnace.

These and other features, objects and advantages of the present invention will become apparent upon reading the following description thereof together with reference to the accompanying drawings.

BRIEF DESCRIPTION OF THE DRAWINGS

FIG. 8 is a partly broken away, vertical cross-sectional view of the structure shown in FIG. 7 taken along section line VIII-VIII of FIG. 3;

FIG. 8A is a top plan view of the gripping arm actuating pistons with one of the arms shown in phantom form;

FIG. 9 is an enlarged fragmentary perspective view, partly broken away, of the linear drive of the shuttle assembly;

FIG. 9A is an enlarged fragmentary cross-sectional view of the drive screw and drive nut for the shuttle;

DETAILED DESCRIPTION OF THE PREFERRED EMBODIMENT

Figure 1:
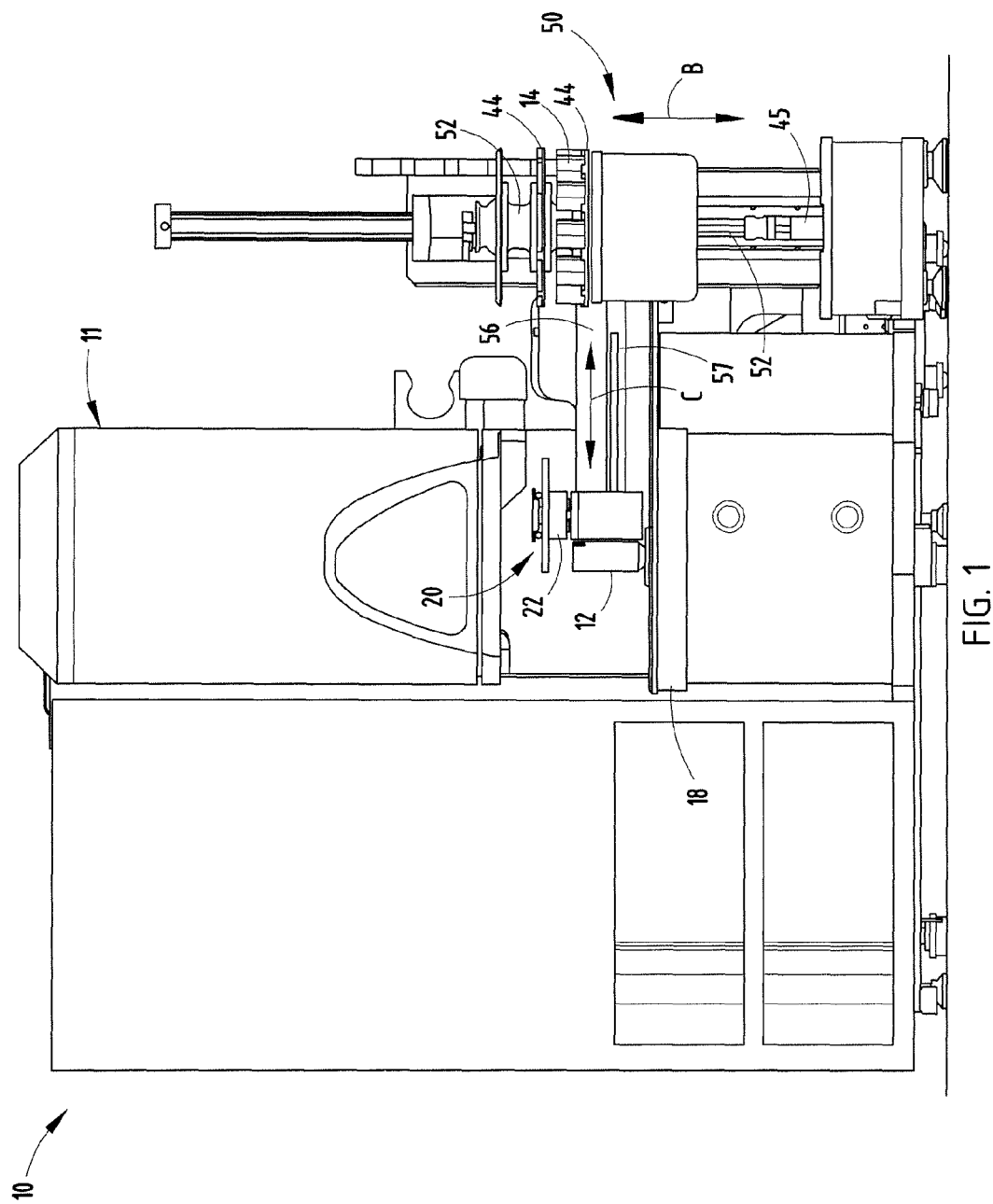
FIG. 1 is a front elevation view of an analyzer including an induction furnace including a crucible loading and unloading shuttle of the present invention together with a crucible loading station.

Referring initially to FIG. 1, there is shown an analyzer 10, such as a Model No. CS600, commercially available from Leco Corporation of St. Joseph, Mich. The analyzer includes an induction furnace 11 and the crucible loading/unloading shuttle assembly 20 of the present invention. Induction furnace 11 includes a crucible-holding pedestal 12, which moves vertically upwardly and downwardly as indicated by arrow A in FIG. 3, to introduce a sample-holding crucible 14 into the furnace for the combustion of and analysis of a specimen held therein. The pedestal is shown in its lowered position in FIGS. 1 and 3-5. A plurality of crucibles 14 each have preloaded and preweighed samples 13 (shown in phantom in FIG. 2) and are held in a vertical sample loading station 50, which may include up to six tiers of crucible-holding disks 44, each including ten crucible-holding sockets. The disks 44 are mounted in vertically spaced relationship on a vertically extending rotary axle 52 which can be raised and lowered, as shown by arrow B in FIGS. 1 and 2, to position a crucible, such as crucible 14' (FIG. 2) to a position to be picked up by gripper arms 26 of shuttle assembly 20. As crucibles 14 are picked from the loading station 50 the disk 44 aligned with the shuttle 16 of shuttle assembly 20 rotates to place the next crucible in position to be picked up. Once a disk 44 is fully unloaded, the shaft 52 is raised by a hydraulic, electric, or pneumatic cylinder 45 (FIG. 1) to position the next fully loaded disk 44 in position to dispense crucibles to shuttle 16.

Figure 7:
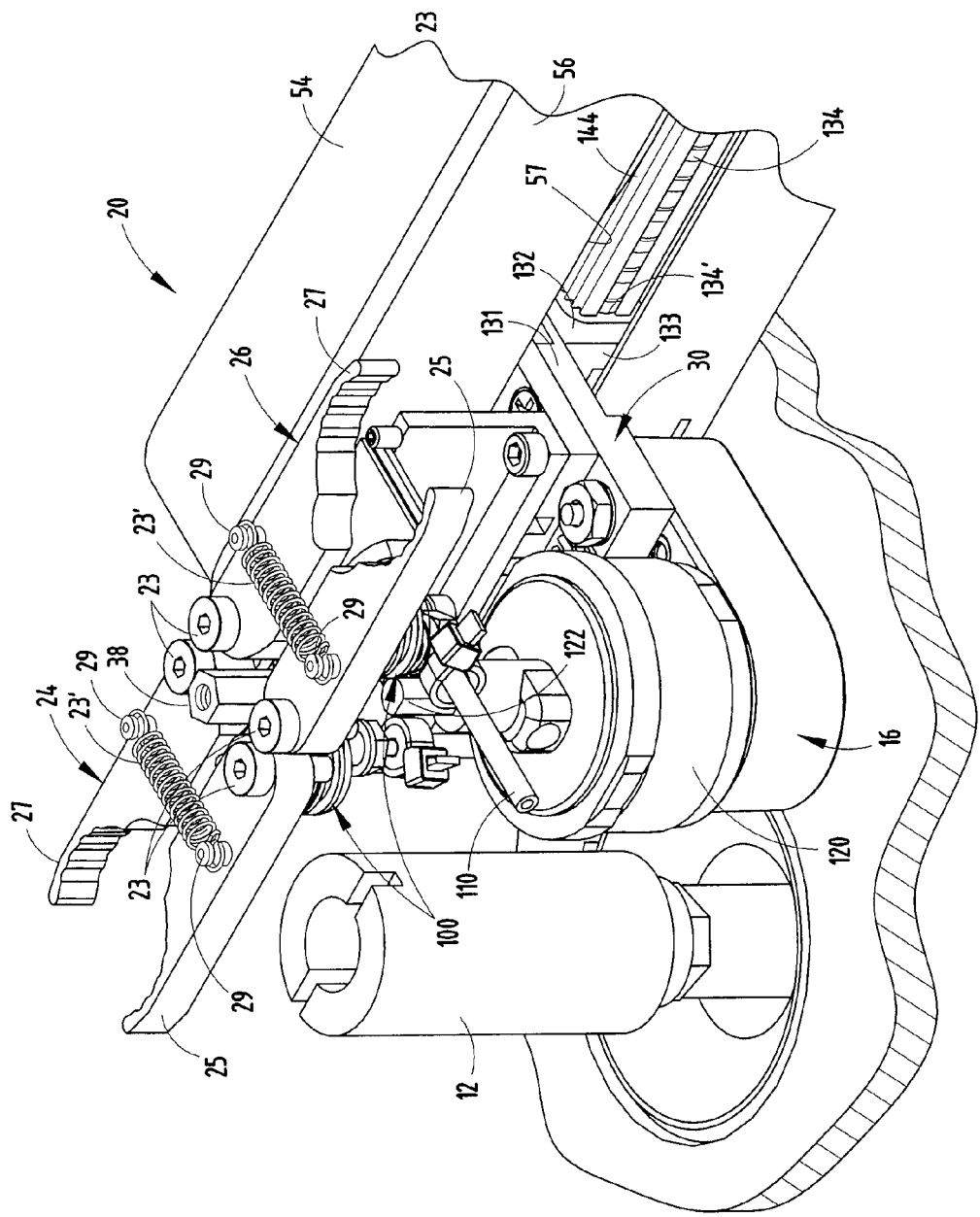
FIG. 7 is an enlarged fragmentary perspective partly broken-away view of the spring-loaded dual gripping arms of the shuttle of the present invention, shown without the housing.

The shuttle assembly 20 includes, as best seen in FIGS. 2-5 and 7, a shuttle 16 with a rotary head 22 to which opposed pairs 24, 26 of spring-loaded, curved facing opposed gripping arms are mounted. Each pair of arms includes arms 25, 27 (best seen in FIG. 7), which are curved to circumscribe opposite sides of a cylindrical crucible 14 to hold crucibles in the shuttle 16 as it linearly moves between the sample loading station 50 in a direction indicated by arrow C in FIGS. 1 and 2 toward and away from furnace pedestal 12. Each of the arms 25, 27 are pivotally mounted to the top 121 of housing 21 (FIG. 8A) of rotary head 22 by pivot pins 23 (FIGS. 7 and 8). Springs 23' are coupled between each arm 25, 27 over posts 29 at a location spaced from their pivot connection to housing 21 of rotary head 22 to urge arms 25, 27 together for gripping the crucibles. The details of the operation of the gripping arms are described below.

Figure 2:
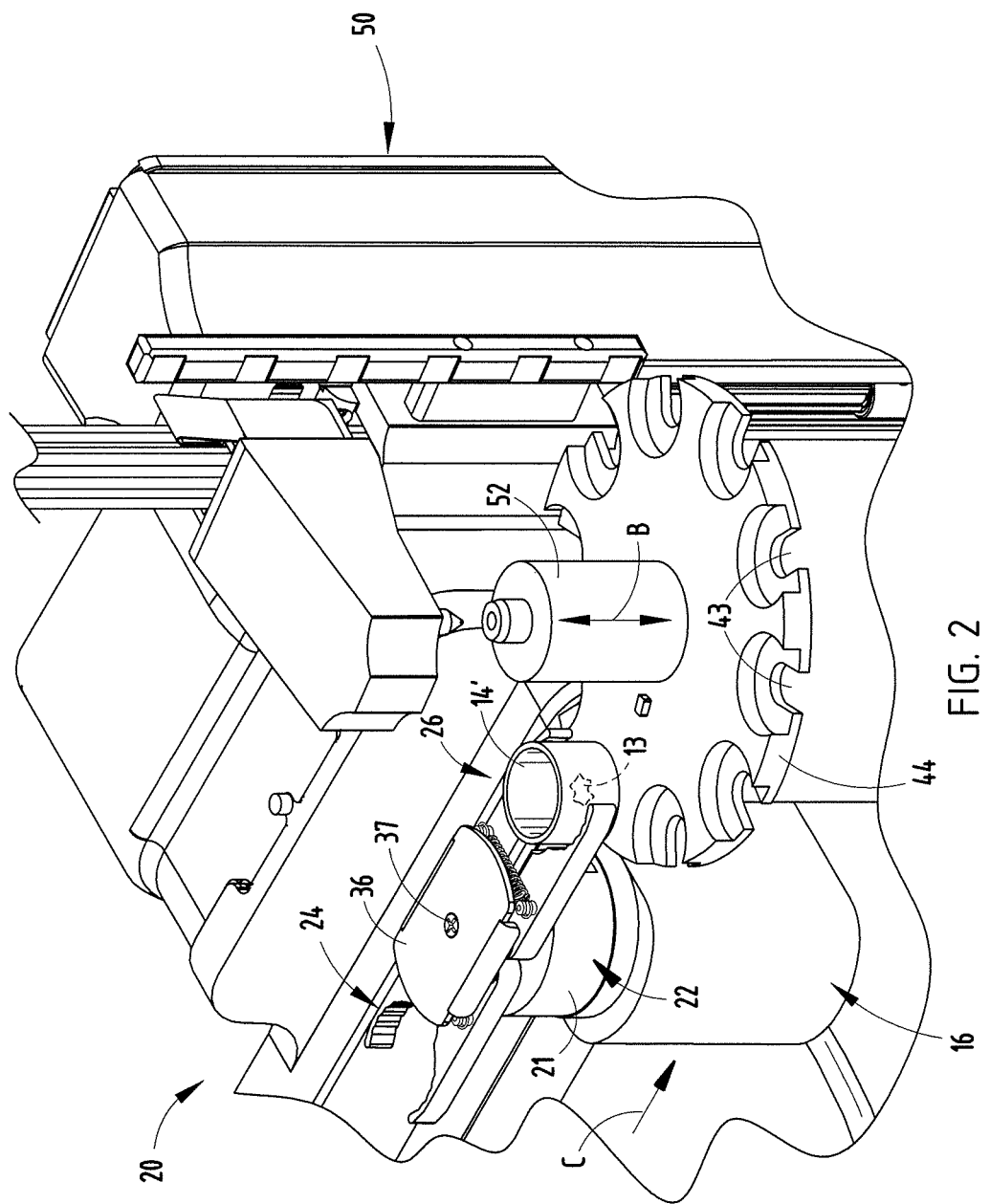
FIG. 2 is a fragmentary perspective view of the structure shown in FIG. 1, shown with the shuttle picking up a new sample-holding crucible from the crucible loading station.
Figure 3:
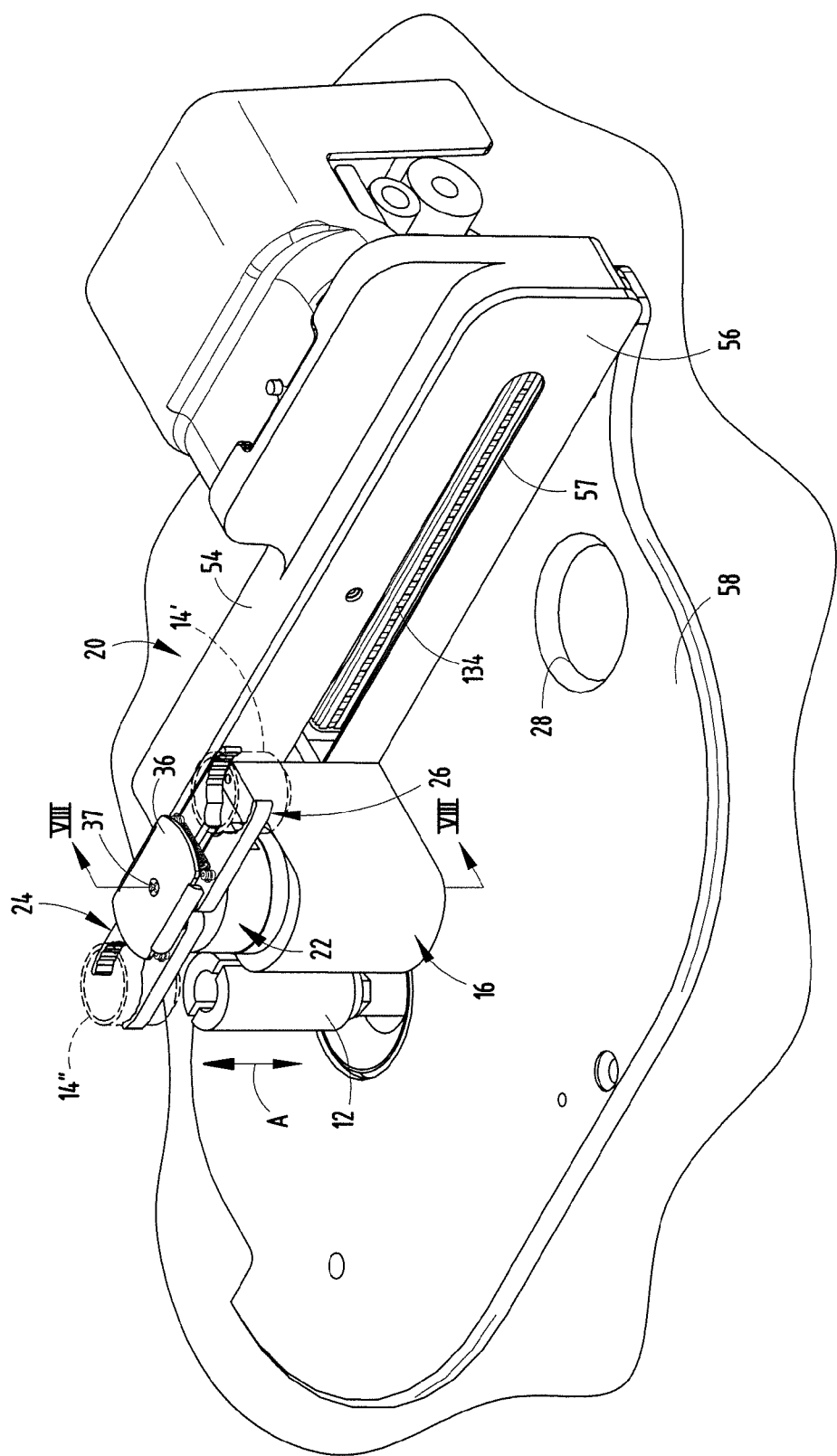
FIG. 3 is a fragmentary perspective view of the structure shown in FIG. 1, shown with the shuttle moved into position picking up a spent crucible from an induction furnace pedestal and about to rotate to place a new sample-holding crucible onto the furnace pedestal.

The shuttle 16 is mounted to a carriage 130 (FIGS. 7-10) for its linear movement between a new crucible picking position (FIG. 2) to the induction furnace pedestal 12, as shown in FIG. 3. Once at pedestal 12, the gripping arms 25, 27 are sequentially actuated to open and pick up the spent crucible 14' as shown in FIG. 3 whereupon the rotary head 22 rotates, as shown by arrow D in FIG. 4, to position the newly picked up crucible 14' onto the pedestal 12, as shown in FIG. 5. After depositing the new sample-holding crucible 14' onto pedestal 12, the shuttle 16 moves from the position shown in FIGS. 3-4 to the intermediate position shown in FIG. 5, whereupon the spent crucible 14' (FIG. 5) is dropped into a discharge chute 28 in base plate 58 by the opening of the gripping arms associated therewith. Subsequently, rotating head 22 of shuttle 16 is again rotated 180° and moved into the right endmost position shown in FIG. 2 to allow arms 26 to pick up the next sample-loaded crucible positioned by the rotation and/or raising of a crucible-holding disk 44 in the rotary crucible loading station 50 to present a new crucible to arms 26. Thus, only the pair of arms 26 engage clean crucibles while only the pair of arms 24 engage contaminated spent crucibles to assure the integrity of the analytical sequence. The method of handling the crucibles including the sequence of operation of the shuttle is now described in conjunction with FIG. 6.

Figure 6:
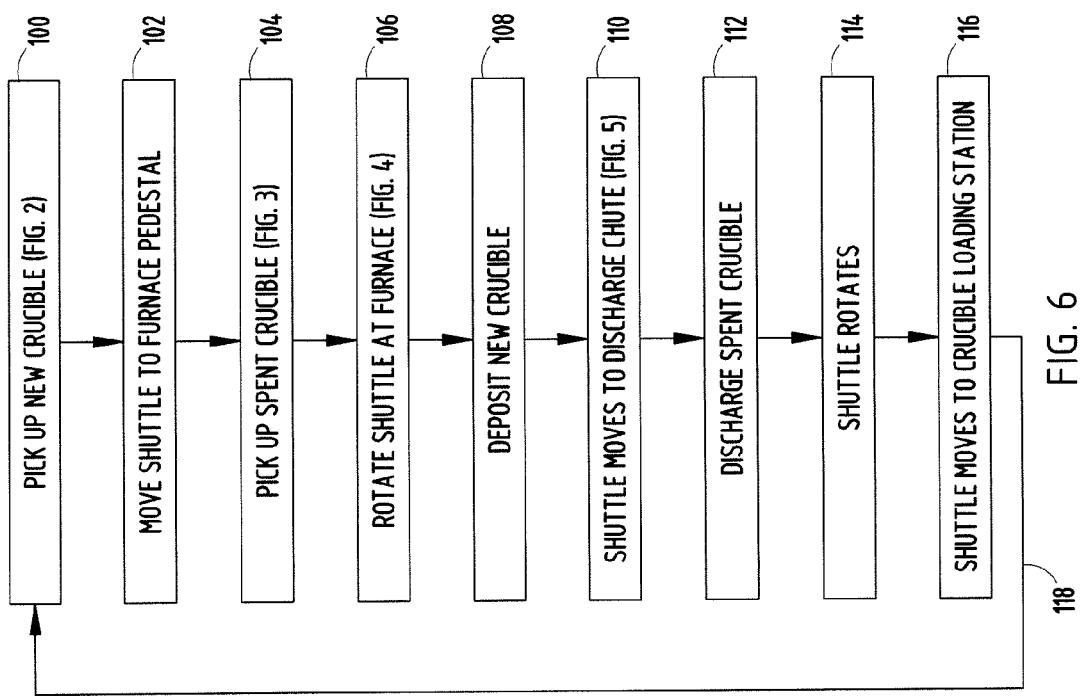
FIG. 6 is a block flow diagram of the method of handling the crucibles with the shuttle of the present invention.

As seen in FIG. 6 block 100, a sample loaded new crucible 14' such as shown in FIG. 2 is picked up by the pair of arms 26 which are opened as described below as the shuttle 16 moves to the loading station 50 to pick up a new sample-holding crucible 14'. The arms are then closed to grip the crucible, and disk 44 is lowered to eliminate any contact between crucible 14' and disk 44. Then, as the shuttle moves away from disk 44 toward the furnace pedestal, the crucible is removed from the slotted holding aperture 43 (FIG. 2) in the crucible-holding disk 44 of loading station 50. The shuttle then moves toward the pedestal 12 as seen by block 102 in FIG. 6 and as it approaches the pedestal with the arms 24 facing the pedestal, the arms are opened to circumscribe a spent crucible on the pedestal which has been lowered automatically from the furnace 11 after an analysis has been completed. The arms 24 then close around the spent crucible 14" and the carriage 130, and rotary head 22 is raised, as described below, to lift the spent crucible 14" off of the pedestal 12 as shown by block 104.

Figure 4:
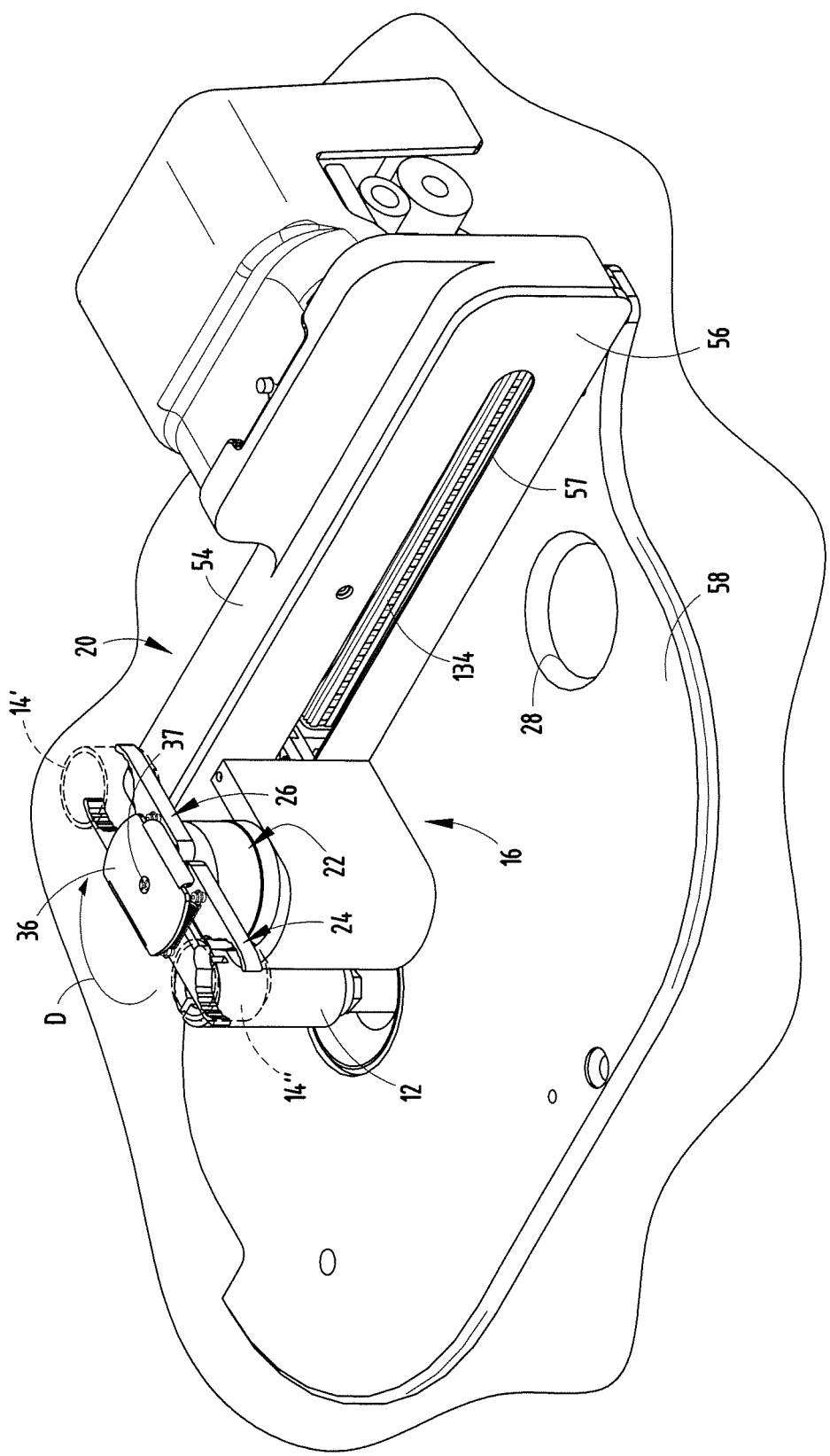
FIG. 4 is a perspective view of the structure shown in FIG. 3, showing the rotation of the shuttle toward a position to position a new crucible on the furnace pedestal.
Figure 5:
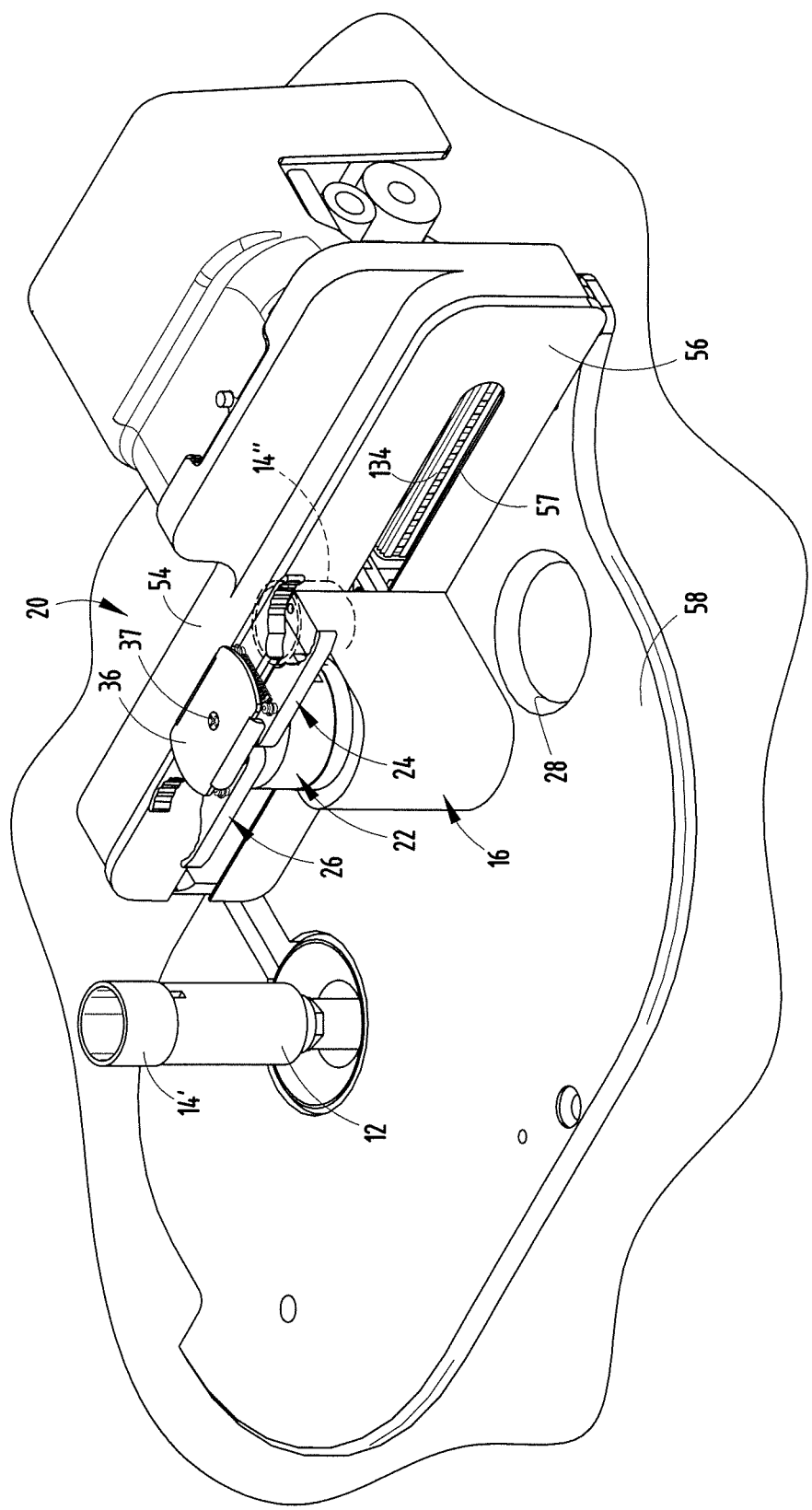
FIG. 5 is a perspective view of the structure shown in FIG. 3 with the new sample loaded crucible placed on the induction furnace pedestal and the spent crucible moved to a position for dropping it into a discharge chute.

The rotary head 22 of shuttle 16 is then rotated 180°, as illustrated in FIG. 4 and represented by block 106. Upon completion of the rotation of head 22, the new crucible 14' is aligned over the pedestal 12 and the rotary head and carriage is lowered to place the crucible 14' on the pedestal at which time arms 26 are opened to deposit the new crucible on the pedestal as shown by block 108. Once this has been done, as show by block 110 and FIG. 5, the shuttle moves to align the spent crucible 14" over the discharge chute 28 in base plate 58. The pair of arms 24 are then opened to drop crucible 14' down chute 28 for disposal as seen by block 112. The rotary head 22 of shuttle 16 is then rotated 180° again to position the pair of arms 26 in a position facing crucible loading station 50 as seen by block 114 and the arms are opened as the shuttle moves to the crucible loading station as shown by block 116 into the position shown in FIG. 2. As seen by line 118 in FIG. 6 the crucible handling sequence is then repeated until all of the crucibles holding samples to be analyzed have been sequentially introduced into the analyzer 10 and an analysis run on the samples. The sequence shown in FIG. 6 is programmed into the microprocessor 72 which is part of the control circuit 70 described below in conjunction with FIG. 13.

Figure 10:
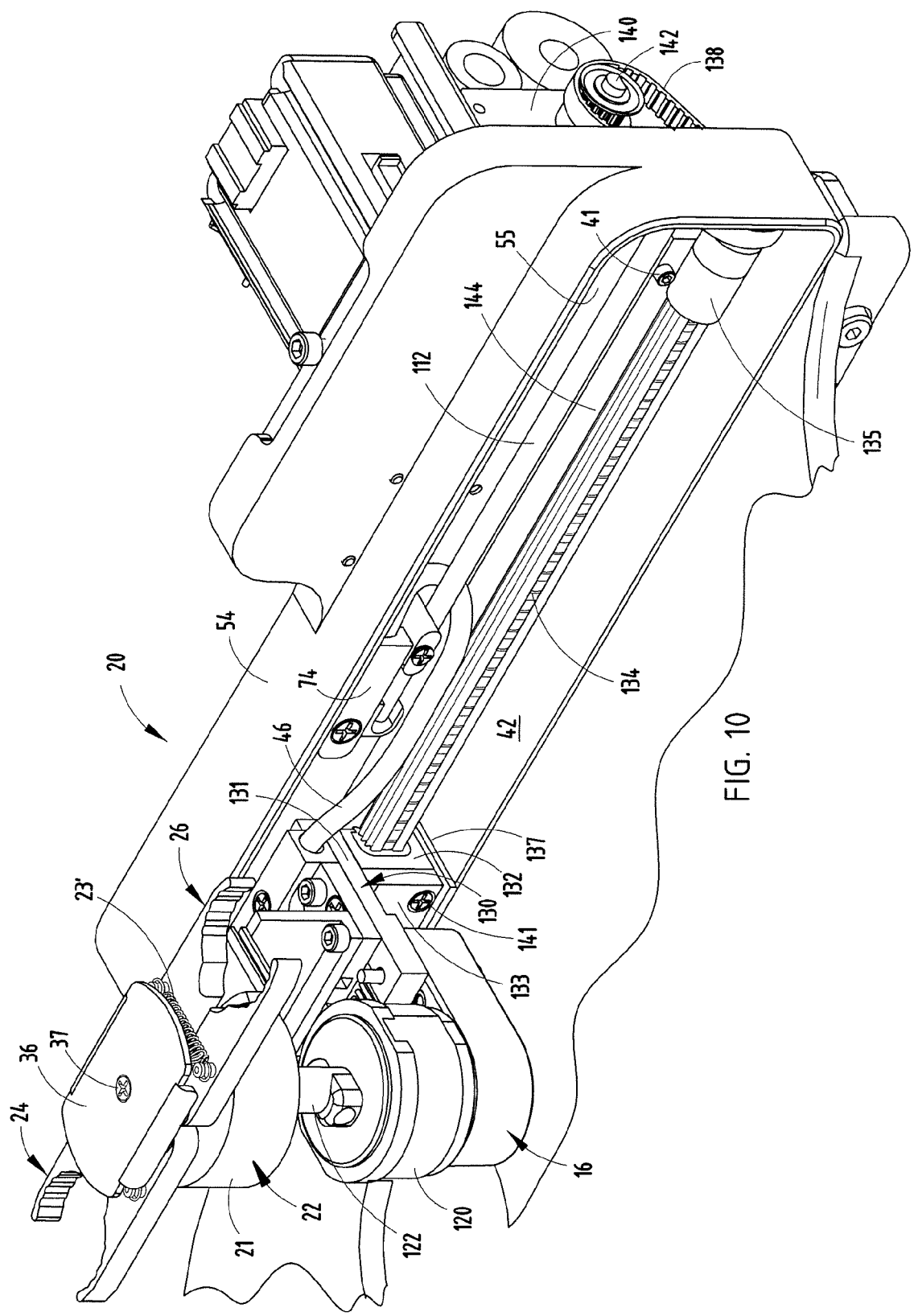
FIG. 10 is an enlarged fragmentary perspective view of the shuttle assembly and housing.

The pairs of gripper arms 24 and 26, each comprising arms 25 and 27, are opened against the force of tension springs 23' holding the arms in a crucible-holding position (shown in FIGS. 3 and 4) by pneumatically actuated, conical actuator pistons 100, as seen in FIG. 7 and best seen in FIGS. 8 and 8A. Springs 23' have ends fitted over posts 29 in arms 25 and 27, as best seen in FIG. 7, to place them in tension. Pistons 100 extend between the pivot arms 25 and 27 at a location between the pivot pins 23 and the spring-holding posts 29. Pistons 100 have a body 102 which is disk shaped and has a peripheral sealing o-ring 109 to movably and sealably mount the pistons within pneumatic cylinders 107 in the rotary head 22. The top 121 (FIGS. 8 and 8A) of rotary head 22 includes a removable cover 105 enclosing pistons 100. Cover 105 has apertures 106 which allow the integral conical tips 103 on the upper side of pistons 100 to extend through head 22, when actuated, to urge pairs of arms 24, 26 to an open crucible releasing position. Tips 103, as seen in FIG. 8A, engage the inner edges 31 of arms 25, 27 acting as a wedge to open the arms to a crucible receiving or releasing position. Pneumatic pressure is selectively applied to each of the piston cylinders 107 and pistons 100 by means of controlled supply lines 108, 110 (FIG. 8). Pistons 100 are returned to a lowered position by compression springs 101 extending between cover 105 (FIGS. 8 and 8A) and the body 102 of the pistons. The pneumatic connection to the pistons 100, as well as the electrical coupling to a rotary actuator 120 (discussed below), is made by a pneumatic and electrical flexible umbilical 46 (FIGS. 9 and 10), which is coupled at one end to shuttle 16 to provide electrical control signals to a rotary actuator 120 and pneumatic pressure individually to pistons 100. Umbilical 46 is allowed to move with the shuttle and is held in an out-of-the-way position from the shuttle drive screw 134 by means of a horizontally extending guide rail 112, as seen in FIGS. 9 and 10. The fixed end of umbilical 46 is coupled to housing 54 by a mounting block 74. The electrical and pneumatic conduits in umbilical 46 are then conventionally coupled to the pneumatic and electrical supplies.

Also mounted to the carriage 130 is a rotary actuator 120 having a vertically extending rotary drive shaft 122 (FIGS. 8-10) coupled to head 22 for reversibly rotating head 22 of shuttle 16 through an arc of 180°. The rotary actuator 120 rotates the rotary head 22 180° in one direction and then reverses direction, such that one pair of gripping arms 26 always handles a new crucible, while the opposite pair of gripping arms 24 handle the contaminated or spent crucibles. The pivoting connections 23 of the pairs of arms 24, 26 are protected by a cover 36 (FIGS. 2-5) by a fastener 37 extending into a vertical post 38, in turn, threaded into a center threaded socket 39 of rotary head 22 (FIG. 8).

Referring now particularly to FIGS. 9-12, the mounting of the shuttle 16 to provide the movement shown in FIGS. 1-5 is described. The shuttle 16 is mounted to a carriage 130 having a polymeric guide block 132 mounted within carriage mounting plate 133 (FIG. 9). The lower surface of carriage mounting plate 133 includes a Teflon® pad 137 which slides along the floor 42 of housing 54. The rotating drive screw 134 is surrounded by an elongated guide 144 secured to back wall 55 of housing 54 by fasteners 41. Guide 144 has an internal bore for receiving drive screw 134 and rotatably supporting the drive screw along its length. The guide 144 also externally slideably receives guide block 132 (as best seen in FIG. 9A), which is secured to plate 133 (FIG. 9) for slideably supporting carriage 130 as it moves between positions shown in FIGS. 2 and 3. The guide block surrounds linear drive screw 134 supported within housing 54 at an end opposite guide block 132 by bearing 135 supported on the back wall 55 of housing 54. The guide block includes a drive nut 134' (FIG. 9A), which drives block 132 and carriage 130 secured thereto by fasteners 141 (FIG. 9) to move the shuttle 16. Elements 132, 134, 135, and 144 can be a commercially available device, such as a rapid drive screw, available from Kerk Motion Products, Inc.

The end of drive screw 134 extends through bearing 135 and is coupled to a gear 136 rotatably driven by a toothed drive belt 138 (best seen in FIG. 9). Belt 138 extends through a slot 139 (FIG. 11) in housing 54 and is coupled to a reversible drive motor 140 through a gear 142 for the reversible rotation of drive screw 134, resulting in the linear movement of carriage 130 between the pedestal 12 and the sample loader 50. The housing 54 for the shuttle assembly 20 includes a front cover plate 56 (FIGS. 1, 3-5, and 7) with a horizontally extending slot 57 to allow an arm 131 (best seen in FIG. 9) coupling shuttle 16 to carriage plate 133 to engage the drive screw 134 throughout the range of movement of the shuttle 16.

Figure 11:
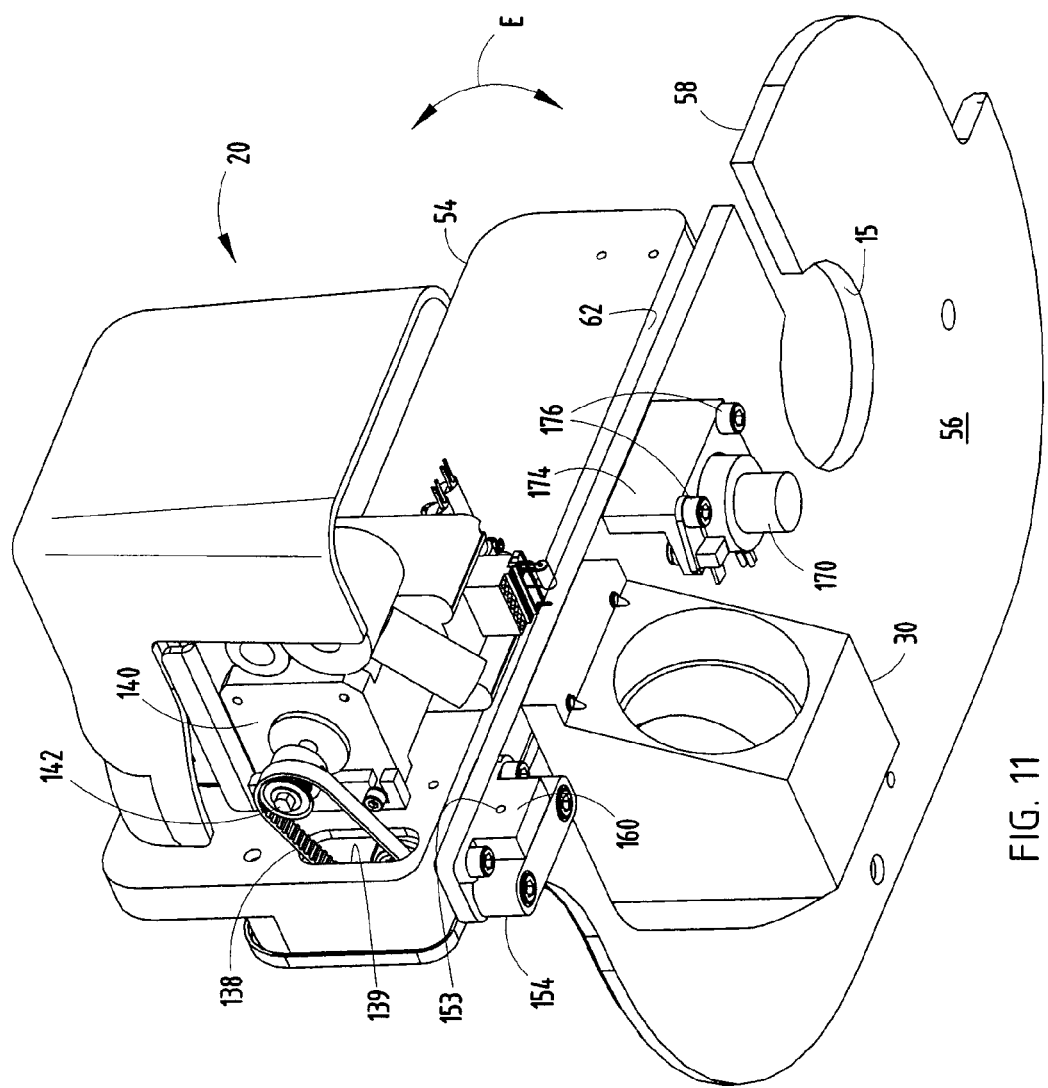
FIG. 11 is a bottom rear perspective view of the shuttle assembly.
Figure 12:
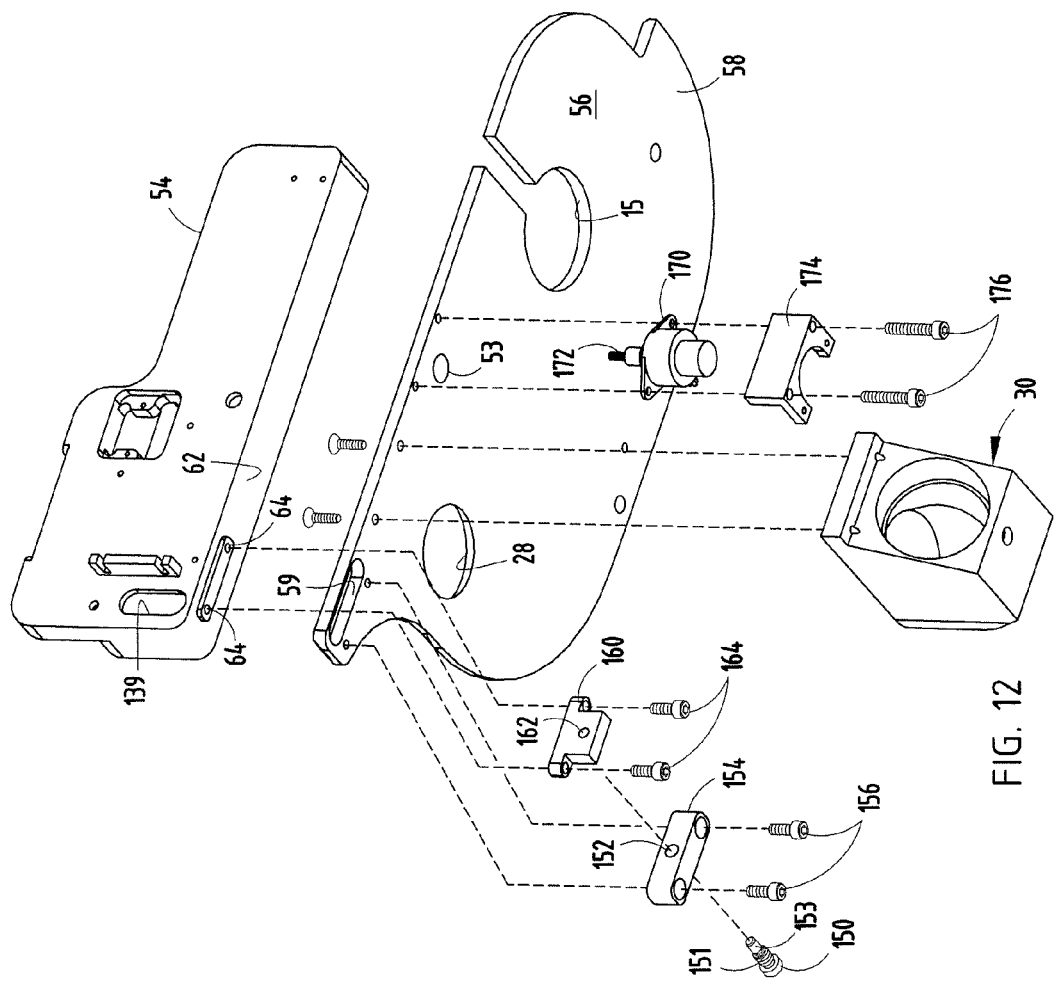
FIG. 12 is an exploded bottom perspective view of a portion of the shuttle assembly showing the pivot mounting of the housing for raising and lowering the gripping arms to lift and place crucibles onto and off of the furnace pedestal.

The shuttle assembly 20, including shuttle 16 with its rotary head 22, gripping arm pairs 24, 26, the shuttle drive mechanism within housing 54, and motor 140, is pivotally mounted to a fixed base plate 58 to be pivotally raised and lowered in a direction indicated by arrow E in FIG. 11 for lifting and placing a crucible from the pairs of arms 24, 26 onto and from the pedestal 12. For such purpose, the mounting housing 54, within which carriage 130 and its drive mechanism are mounted, are pivotally mounted about a pivot axle 150 (FIG. 12). Axle 150 includes a section 151 which extends through an aperture 152 in a mounting block 154. Block 154 is secured by fasteners 156 to the lower surface 56 of plate 58 adjacent an aperture 59 in plate 58. Axle 150 has an end 153 which extends into a threaded aperture 162 in a T-shaped pivot block 160 which is secure to the outer bottom surface 62 of housing 54 by fasteners 164 extending into threaded sockets 64. Block 160 extends through aperture 59 when housing 54 is attached to base plate 58. Aperture 162 in block 160 aligns with aperture 152 in adjacent block 154. When pivot axle 150 is threaded into aperture 162, end 151 of axle 150 provides a pivot correction between housing 54 and its attached components with respect to base plate 58, as seen in FIG. 11.

A linear actuator 170 is mounted in spaced relationship to pivot pin 150 and has a linearly movable shaft 172 which engages the lower surface 62 of housing 54 through opening 53 in base plate 58. Actuator 170 is secured to the underside 56 of plate 58 by a mounting bracket 174 and threaded fasteners 176 (FIG. 12). When actuator 170 is activated, housing 54 pivots upwardly raising the carriage 130 and shutter 16 with gripping arm pairs 24 and 26 upwardly a distance sufficient to lift a crucible off of the pedestal 12. Thus, the rotating head 22 lifts to pick up a spent crucible and rotates and then lowers to deposit a new crucible on pedestal 12. It then moves and opens to discharge the spent crucible into discharge chute 28. The shuttle head 22 then rotates, and the shuttle is moved to the sample loading station 50 where it picks up a new crucible and again moves toward the pedestal 12 where it picks up the spent crucible to repeat the cycle. Plate 58, as seen in FIGS. 3, 4, 11, and 12, includes a slotted aperture 15 for surrounding the furnace pedestal 12 and is secured to the frame 18 (FIG. 1) of furnace 11 in a conventional manner. Mounted to discharge chute 28 (FIGS. 3-5) is an elbow 30 (FIGS. 12 and 13) for directing spent crucibles toward a disposal bin (not shown). Motor 140 is enclosed by a suitable cover 32 (FIGS. 3-5, 10, and 11).

Figure 13:
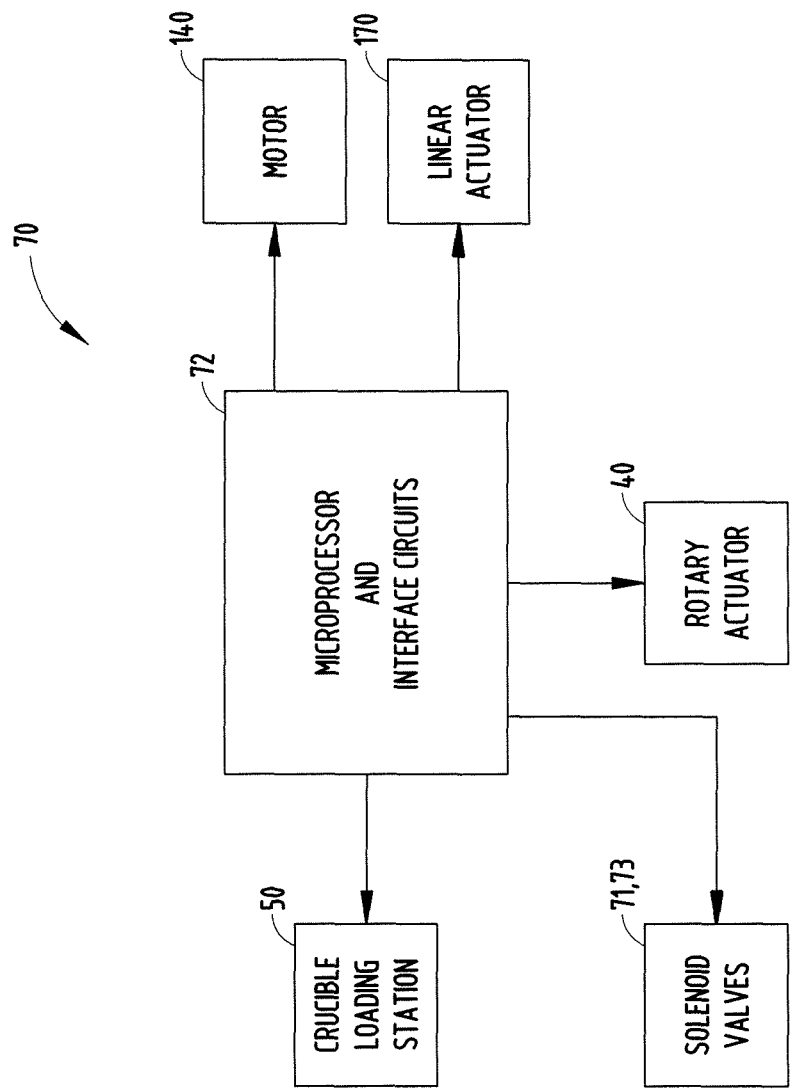
FIG. 13 is an electrical circuit diagram in block form of the control circuit for the system of the present invention.

FIG. 13 is a block electrical diagram of a control circuit 70 for controlling the shuttle assembly 20 in its sequence of operation as described above with reference to FIG. 6. Circuit 70 includes a microprocessor 72 and suitable memory and interface circuits which couple to the drive motor 140 and linear actuator 170 for raising, lowering, and transporting crucibles. Circuit 70 also provides timed signals to rotary actuator 120 to rotate the rotary head 22 of shuttle 16. Microprocessor 72 also actuates the solenoid valves 71 and 73 for actuating the pneumatic supply to control pistons 100 (FIG. 8) for sequentially opening and closing the gripper arm pairs 24 and 26 for alternatively gripping and releasing crucibles therein. The control circuit 70 can be incorporated into the overall control for the instrument 10 and furnace 11 with which the crucible loading and unloading system is mounted including the control of the sample loading station 50.

With this system, sample-holding crucibles can be picked up from a loading station, transported to the induction furnace pedestal whereupon a spent crucible is picked up, the assembly rotated to deposit a new crucible onto the induction furnace pedestal and moved to an intermediate position for discharging the spent crucible and subsequently rotated and moved again to the loading station. By providing opposed gripping arms which are rotated for picking up and discharging crucibles from an induction furnace, the throughput of sample-holding crucibles is greatly improved. This mechanism can also be used for moving crucibles or other articles between first and second positions. As an example, a similar crucible handling assembly can be used to load crucibles onto station 50 from a sample weighing balance.

FIGS. 14-21 show a modified crucible shuttle assembly in which the shuttle 16' is plugged into and easily removable from the carriage assembly 130'. This allows the quick removal for maintenance or replacement of the shuttle. In addition, the pivoted raising and lowering mechanism for the shuttle employed for picking up crucibles at a crucible unloading station and lowering them into a furnace has been replaced with a vertically movable assembly best shown in FIGS. 14C, 20, and 21. These are the major changes to the previous embodiments of the invention described above. Like or equivalent structural elements are identified by the same reference numerals as in the previous drawings. New or somewhat different structure is identified by a prime (') symbol or by the prefix "2" for 200 series elements.

Figure 14A:
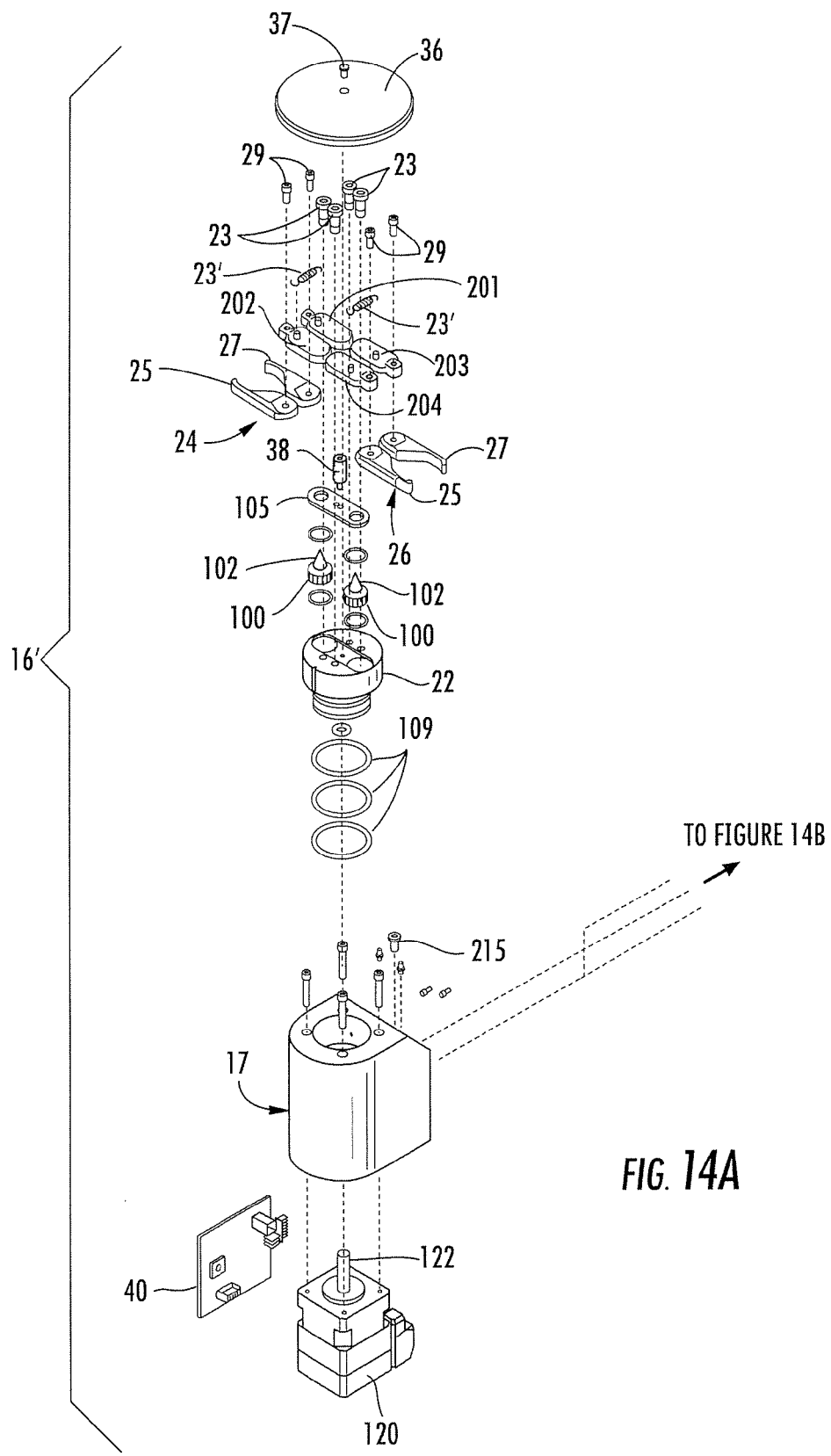
FIGS. 14A-14C is an exploded perspective view of an alternative embodiment of the shuttle and carriage showing the quick disconnect connection between the two assemblies.
Figure 15:
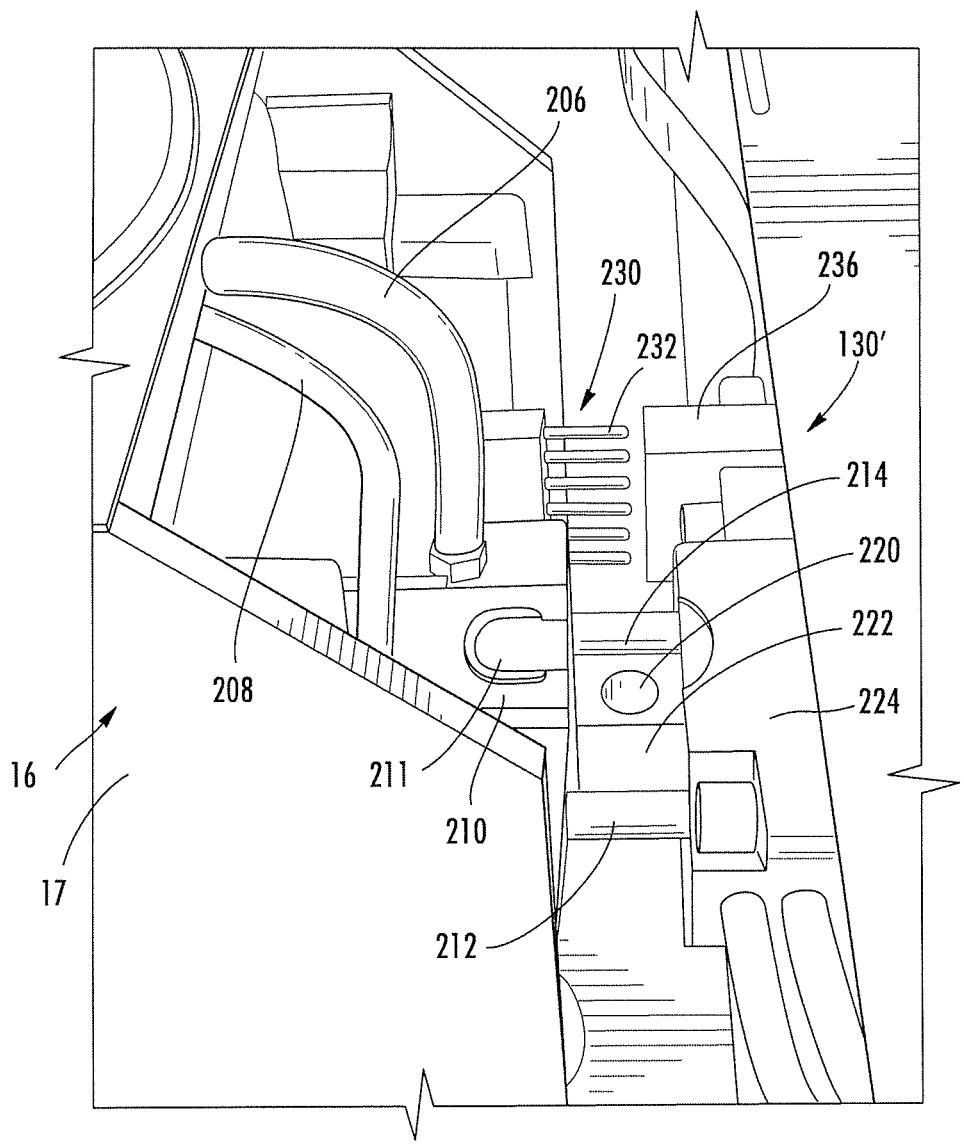
FIG. 15 is a fragmentary upper perspective view of the shuttle and carriage shown with the shuttle being unplugged from the carriage.
Figure 18:
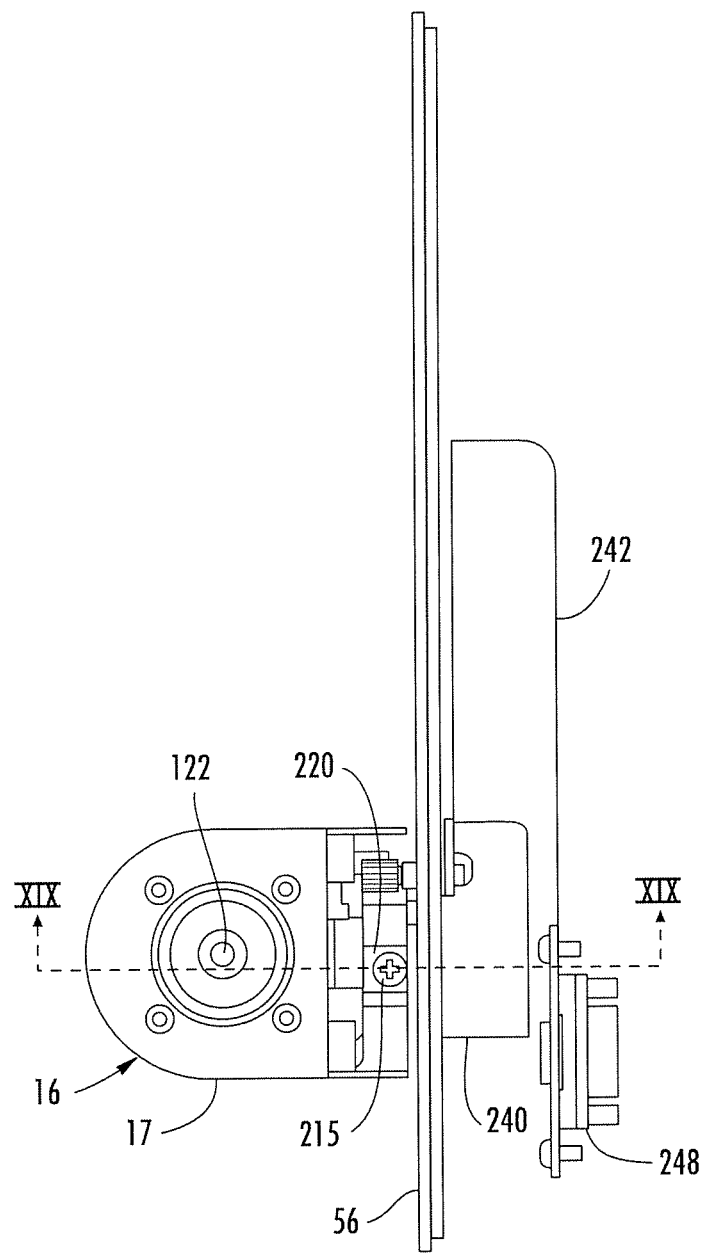
FIG. 18 is a top plan view of the carriage and shuttle.
Figure 19:
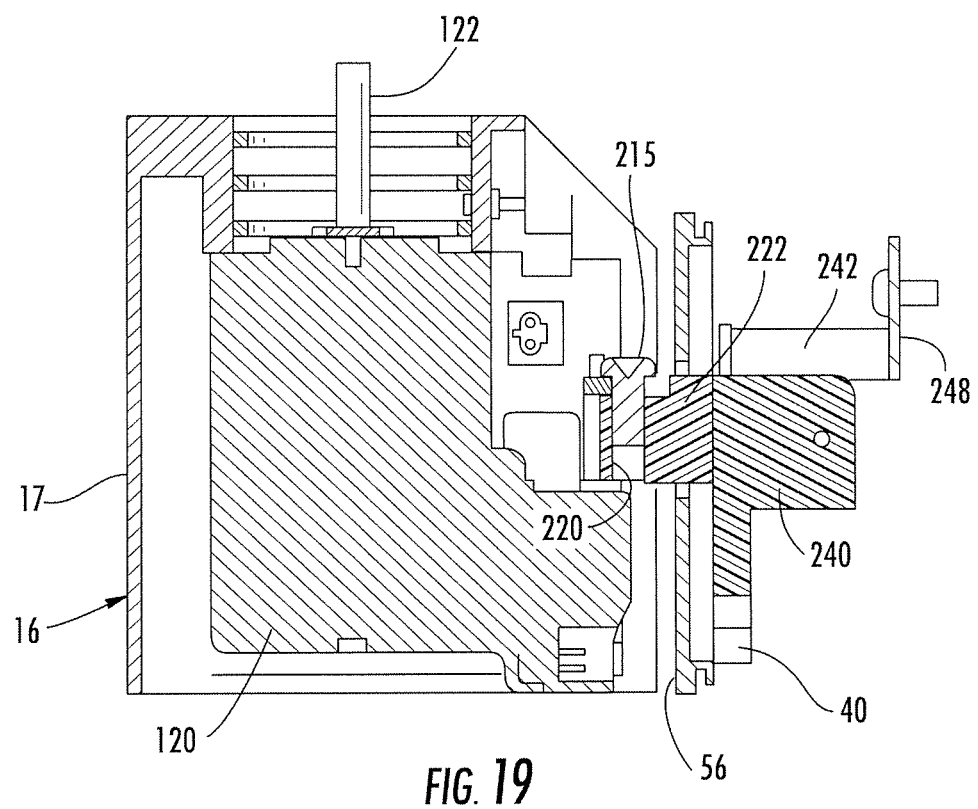
FIG. 19 is a cross-sectional view of the carriage and shuttle taken along section line XIX-XIX of FIG. 18.

In FIG. 14A, changes to the structure disclosed in the earlier figures includes four links 201-204 which couple the pickup arms 24 and 26 to the rotary head 22 of the shuttle 16'. Links 201-204 have their outer ends pivotally coupled to pairs of arms 24, 26 and their inner ends pivotally coupled to rotary head 22. The plug-in coupling of the shuttle 16' to the carriage 130' is illustrated in FIG. 15, which shows housing 17 for the shuttle 16' with pneumatic connections 206 and 208 leading from a pneumatic connection block 210. Block 210 includes connectors 212 and 214 which removably and sealably mate with apertures 223 and 225 (FIG. 16) of transition block 224 of carriage 130'. Block 210 includes a slot 211 (FIG. 17) for receiving a locking screw 215 (FIGS. 14A, 18 and 19). Once shuttle 16' is inserted or plugged into carriage 130', screw 215 is inserted into a threaded aperture 220 (FIGS. 15 and 19) of plug 222 of the transition block 224 extending between the shuttle 16' and carriage 130'. Block 210 also includes an aperture 223' (FIG. 17) defining a socket which matingly receives plug 222, it being understood that the plug and socket can be reversed on the two mating parts. The plug 222 and socket 223 provide, together with locking screw 215, a secure mechanical connection of the shuttle 16' to the carriage 130', which can be readily disconnected for servicing.

The plug-in shuttle 16' also includes an electrical connector 230 with pins 232 that plug within the receiving apertures 234 of electrical socket 236 mounted on the carriage sliding block 240, as best seen in FIGS. 14B and 15-17. Thus, as seen in FIGS. 14-17, the shuttle 16' has a quick disconnect plug-in relationship with carriage 130' in which mechanical, electrical, and pneumatic connections are made. This greatly facilitates the quick removal of the shuttle for repair or replacement and reduces the downtime for the instrument. The electrical connections provide electrical power for actuating rotary motor 120 while the pneumatic connections serve to actuate the pistons 100 as in the first embodiment.

Figure 14B:
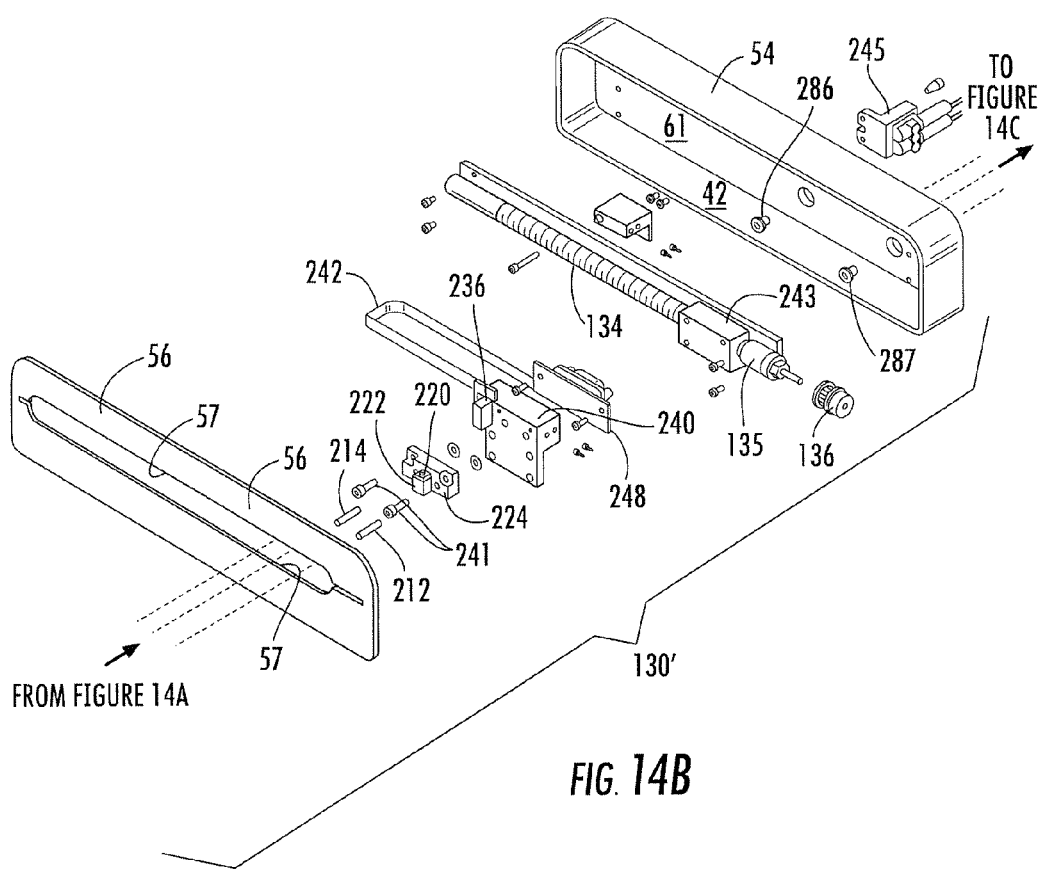
Figure 16:
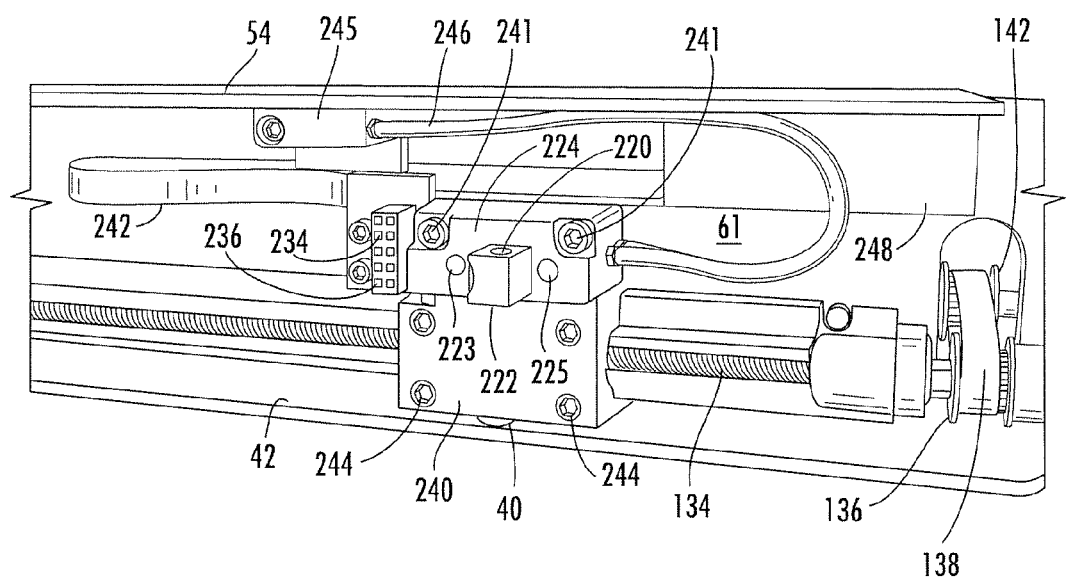
FIG. 16 is a front elevation view of the carriage showing the plug-in connection elements for the shuttle.
Figure 17:
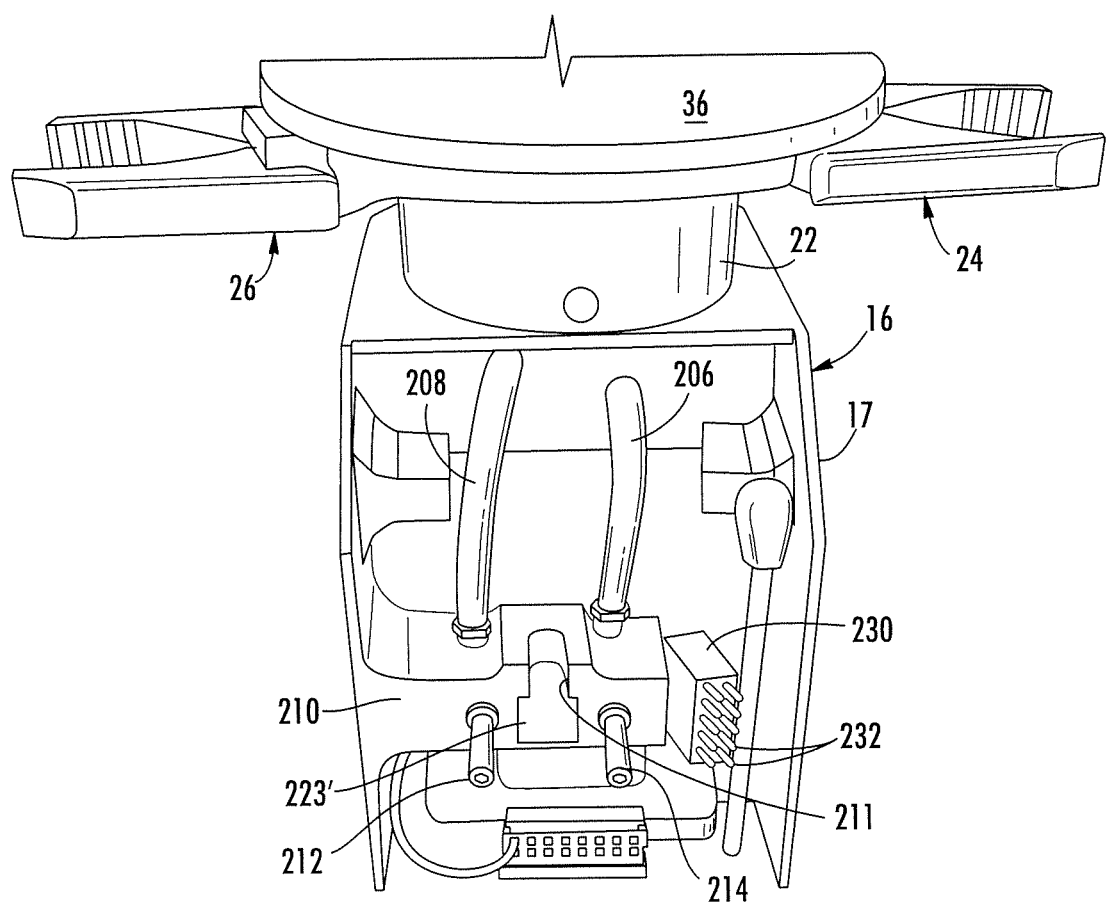
FIG. 17 is a front elevation view of the side of the shuttle facing the carriage showing the plug-in connection elements for the carriage.

As in the previous embodiment of the invention, the carriage 130' includes a rotating drive screw 134 and thrust bearing 135 coupled to a mounting block 243. As seen in FIGS. 14B and 16, the transition block 224 is secured to sliding block 240 by fasteners 241. Block 240, in turn, is secured to mounting block 243 by fastening screws 244. As screw 134 is rotated by the drive motor 140 and drive belt 138 through gears 136, 142, block 243 and the shuttle 16' mounted thereto move between the furnace 11 and crucible loading station 50. Block 240 includes a roller 40 which rides along the lower surface 42 of housing 54 to provide additional support for the shuttle 16' plugged into the carriage 130'.

The electrical socket 236 is coupled to the instrument control circuit 72 (FIG. 13) by a flex circuit 242 which comprises electrical conductors printed on a Kapton® or Mylar® substrate. Flex circuit 242 has one end coupled to socket 236 and an opposite end coupled to an interface circuit 248 (FIG. 14B) mounted to the rear wall 61 of housing 54. Circuit 248 is coupled to the main control circuit 72 through a conventional interface.

A pneumatic source is coupled by a manifold 245 (FIGS. 14B and 16) to which a fused pair of hoses 246 are coupled and extend to sliding block 240 and the transition block 224 and communicate with apertures 223 and 225, in turn, coupled to the shuttle 16' as discussed above. The flex circuit 242 and dual hose 246 provides unobstructed motion for the sliding block 240 as it travels along the length of jack screw 134 between the furnace and the crucible loading station, as shown by arrow C in FIG. 1. In place of the pivot raising and lowering of the shuttle 16', the shuttle is vertically and linearly raised and lowered by the assembly shown in FIGS. 14C, 20, and 21 now described.

Figure 21:
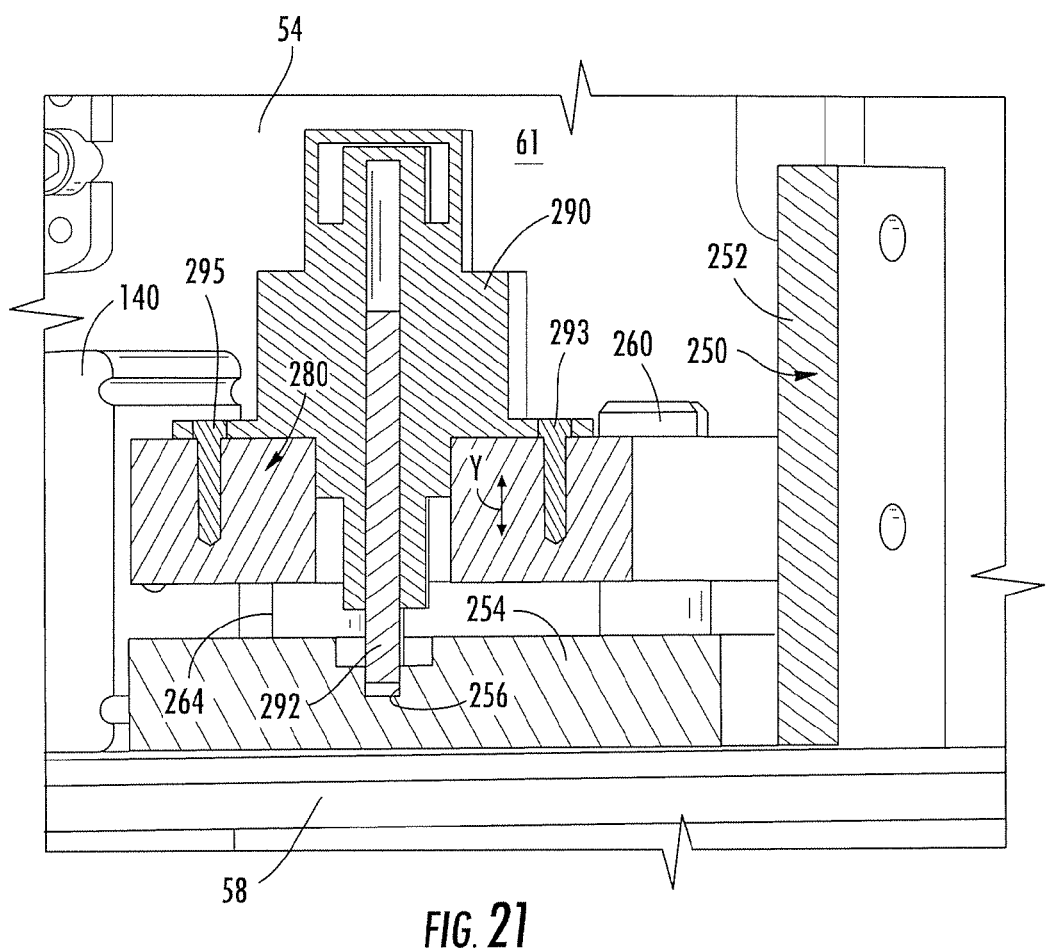
FIG. 21 is a vertical cross-sectional view of the lifting platform assembly shown in FIG. 20.

A fixed L-shaped mounting bracket 250 has a base plate 254 which is secured to the horizontal plate 58 of the analyzer (FIGS. 5 and 21). Bracket 250 has an upstanding leg 252 also coupled to the instrument (not shown). Suitable fasteners, such as screws, extend through apertures 251 in bracket 250

Figure 14C:
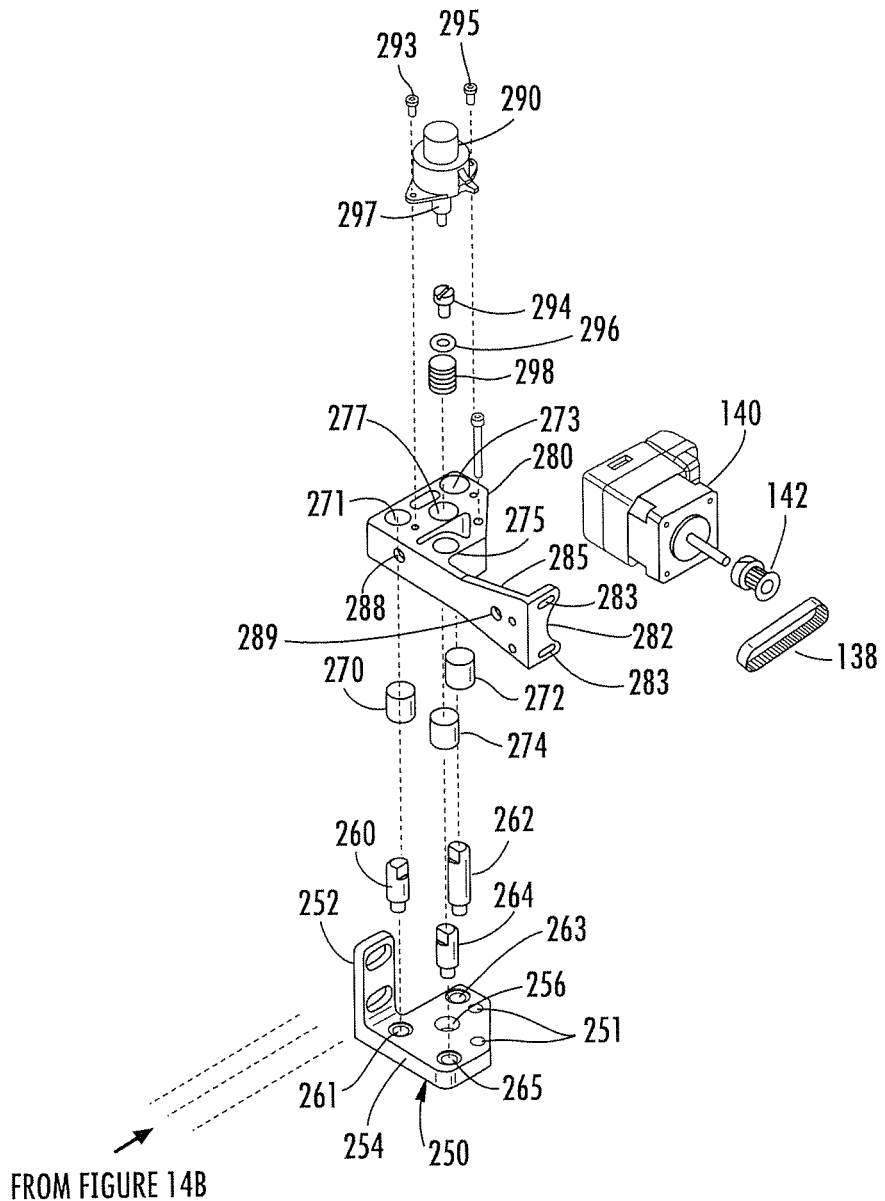
Figure 20:
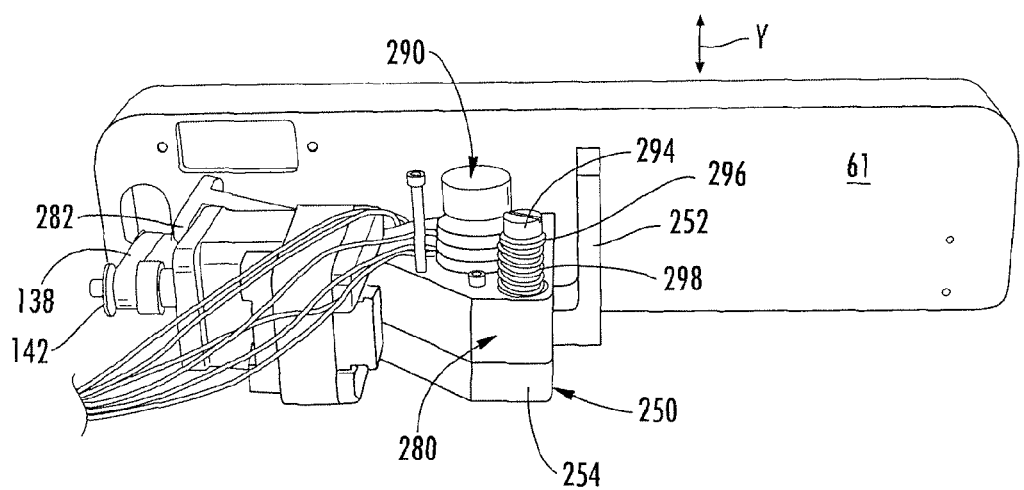
FIG. 20 is a rear perspective view of the carriage showing the lifting platform assembly for raising and lowering the carriage and shuttle attached thereto.

(FIG. 14C) to secure the bracket base 254 to the instrument support plate 58. Three guide rods 260, 262, and 264 with reduced diameter lower ends are conventionally secured within apertures 261, 263 and 265 of base 254. These guide rods 260, 262, and 264 extend vertically and are surrounded by bushings 270, 272, and 274 which, in turn, extend through apertures 271, 273, and 275 in a vertically movable bracket 280. Motor 140 is secured at an L-shaped end 282 of movable bracket 280, which includes apertures 283 for receiving fasteners, such as screws, therethrough. This secures motor 140 within the U-shaped slot 285 of bracket 280, as seen in FIG. 20. Bracket 280 is also fixedly mounted to the rear wall 61 of housing 54 by means of a pair of screws 286 and 287 (FIG. 14B) which extend into threaded apertures 288 and 289 of bracket 280, as seen in FIG. 14C.

Bracket 280 slides vertically guided by rods 260, 262, 264 and bushings 270, 272, 274 (as indicated by arrow Y in FIGS. 20-21) with respect to the instrument base 58. To provide such motion, a linear actuator 290 is fixedly mounted to the upper surface of bracket 280 by means of a pair of mounting screws 293, 295 (FIG. 21). Actuator 290 has an extendable shaft 292 with an end that extends into aperture 256 in plate 254 (FIGS. 14C and 21). As shaft 292 of linear actuator 290 extends and retracts, bracket 280 moves upwardly and downwardly raising and lowering the shuttle 16' attached to carriage 130' a distance sufficient for picking up a crucible from the crucible loading station 50 (FIG. 1) and lower the crucible into the furnace 11, such as illustrated in FIG. 5. The movable bracket 280 is held in a normally lowered position by means of a spring-biased hold-down screw 294 (FIG. 20), which includes a washer 296 and compression spring 298 to urge bracket 280 to a normally downward position. It is raised to a crucible picking-up position by means of the actuator 290 when shaft 292 of the actuator is extended. The shaft 292 of actuator 290 extends through a clearance aperture 277 in bracket 280, such that it is free to extend and retract.

Thus, with the system of the present invention, not only is the shuttle 16' easily removable from the carriage 130', the carriage is moved vertically with respect to the base of the instrument, allowing the use of a crucible loading station which does not need to raise and lower for picking up a crucible for transfer to the furnace. Finally, the use of a printed flex circuit on a Kapton® or Mylar® substrate eliminates the use of bundled wires and provides unobstructed movement, together with the dual pneumatic hose, of the shuttle along the carriage.

It will become apparent to those skilled in the art that various modifications to the preferred embodiment of the invention as described herein can be made without departing from the spirit or scope of the invention as defined by the appended claims.

The invention claimed is:

1. A shuttle system for loading and unloading crucibles to and from a furnace associated with an analyzer and a crucible loading station comprising:
    a shuttle including pairs of opposed crucible-gripping arms for selectively gripping crucibles on opposite sides of an axis of rotation;
    a rotating head mounted to said shuttle for supporting said pairs of arms;
    a carriage coupled to said shuttle for moving said shuttle between a furnace and a loading station for providing sample-holding crucibles for introduction into said furnace;
    a linear guide for only translation of the carriage between said furnace and said loading station; and
    wherein an improvement comprises a plug-in connection between said shuttle and said carriage, wherein said shuttle includes plug-in pneumatic and electrical connections to said carriage.

2. The system as defined in claim 1 wherein said carriage includes a drive screw and a mounting block assembly coupled to said drive screw for movement of said block between a furnace area and a loading station, and wherein said block includes one of an electrical plug and socket and said shuttle includes the other of an electrical plug and socket such that said shuttle can be electrically plugged into said block.

3. The system as defined in claim 2 wherein said block includes a pneumatic connection and said shuttle includes a mating pneumatic connection which is disconnectable from said pneumatic connection of said block such that said shuttle can be unplugged from said block.

4. The system as defined in claim 3 wherein said block includes one of an extending tab and socket and said shuttle includes the other of an extending tab and socket such that said shuttle can be mechanically plugged into said block of said carriage.

5. The system as defined in claim 4 and further including a locking screw coupled between said block and said shuttle for locking said shuttle to said block once plugged into said block.

6. The system as defined in claim 5 wherein said carriage further includes a flat flexible electrical ribbon conductor coupled at one end to said one of a plug and socket of said block and at an opposite end to a fixed circuit to supply electrical signals to said moving block and said shuttle.

7. The system as defined in claim 6 wherein said carriage further includes a flexible pneumatic hose coupled at one end to said connection of said block and at an opposite end to a pneumatic source for supplying pressure to said moving block and said shuttle plugged into said moving block.

8. The system as defined in claim 7 and further including actuators for selectively opening at least one arm of said pairs of gripping arms to grip and release crucibles.

9. The system as defined in claim 1 and further including a mechanism coupled to said carriage for selectively raising and lowering said shuttle coupled to said carriage.

10. The system as defined in claim 9 wherein said mechanism comprises a fixed base plate, a movable bracket coupled to said carriage, guide rods extending between said movable bracket and said base plate, and an actuator coupled between said movable bracket and said base plate for raising and lowering said carriage and said shuttle coupled to said carriage.

11. The system as defined in claim 10 wherein said actuator is a linear actuator.

12. A system for moving articles between at least first and second spaced-apart positions comprising:
    a shuttle supporting opposed gripping arms for gripping articles, said shuttle including at least one pneumatic actuator and at least one electrical actuator;
    a carriage for only linearly moving said shuttle between a first position and a second position for picking up and moving articles, said carriage including a sliding block having a supply of electrical signals and a pneumatic source coupled thereto; and
    said shuttle including one of a plug and socket and said sliding block of said carriage including a mating one of the other of a plug and socket such that said shuttle receives pressure for said pneumatic actuator and electrical signals for said electrical actuator from said carriage when said shuttle is plugged into said sliding block and said carriage moves said shuttle.

13. The system as defined in claim 12 wherein said supply of electrical signals includes a flex circuit coupled at one end to a fixed interface circuit and at the other end to said one of said plug and socket on said sliding block.

14. The system as defined in claim 13 wherein said pneumatic source of said carriage includes a flexible tube coupled at one end to a fixed pneumatic manifold and at an opposite end to one of a pneumatic plug and socket on said sliding block.

15. The system as defined in claim 14 wherein said sliding block includes one of a mechanical plug and socket and said shuttle includes a mating one of the other of a plug and socket for mechanically securing said shuttle to said sliding block of said carriage.

16. The system as defined in claim 15 and further including a locking screw coupled between said block and said shuttle for locking said shuttle to said block once plugged into said block.

* * * * *

UNITED STATES PATENT AND TRADEMARK OFFICE
CERTIFICATE OF CORRECTION

| | | |
|---|---|---|
| PATENT NO. | : 8,657,550 B2 | Page 1 of 1 |
| APPLICATION NO. | : 13/032844 | |
| DATED | : February 25, 2014 | |
| INVENTOR(S) | : Ford et al. | |

It is certified that error appears in the above-identified patent and that said Letters Patent is hereby corrected as shown below:

In the Specification

Column 1, line 52, insert --of-- after --amount--;

Column 4, lines 26 and 32, "14'" should be --14"--;

Column 5, line 5, "show" should be --shown--;

Column 5, line 7, "14'" should be --14"--;

Column 6, line 54, "secure" should be --secured--;

Column 6, line 60, "correction" should be --connection--; and

Column 8, line 56, "provides" should be --provide--.

Signed and Sealed this
Eighteenth Day of November, 2014

Michelle K. Lee
*Deputy Director of the United States Patent and Trademark Office*